(12) United States Patent
Sabolich et al.

(10) Patent No.: US 6,500,210 B1
(45) Date of Patent: Dec. 31, 2002

(54) SYSTEM AND METHOD FOR PROVIDING A SENSE OF FEEL IN A PROSTHETIC OR SENSORY IMPAIRED LIMB

(75) Inventors: John A. Sabolich, Oklahoma City, OK (US); Giovani M. Ortega, Oklahoma City, OK (US); G. Blaine Schwabe, IV, Oklahoma City, OK (US)

(73) Assignee: Seattle Systems, Inc., Poulsbo, WA (US)

( * ) Notice: Subject to any disclaimer, the term of this patent is extended or adjusted under 35 U.S.C. 154(b) by 1046 days.

(21) Appl. No.: 08/763,012

(22) Filed: Dec. 10, 1996

Related U.S. Application Data

(63) Continuation-in-part of application No. 08/281,491, filed on Jul. 27, 1994, now abandoned, which is a continuation of application No. 07/942,205, filed on Sep. 8, 1992, now abandoned.

(51) Int. Cl.$^7$ .................................................. A61F 2/70
(52) U.S. Cl. ...................................................... 623/24
(58) Field of Search ............................ 623/24, 25, 27, 623/57; 600/592; 414/5; 73/172, 769, 771, 772, 865.4

(56) References Cited

U.S. PATENT DOCUMENTS

| | | |
|---|---|---|
| 1,113,366 A | 10/1914 | Miller |
| 3,273,559 A | 9/1966 | Evans |
| 3,323,358 A | 6/1967 | Fraioli |
| 3,344,792 A | 10/1967 | Offner et al. |
| 3,722,005 A | 3/1973 | Cowland |
| 3,751,733 A | 8/1973 | Fletcher et al. |
| 3,820,168 A | 6/1974 | Horvath |
| 3,940,803 A | 3/1976 | Weis, Jr. et al. |
| 4,195,643 A | 4/1980 | Pratt, Jr. |
| 4,387,472 A | 6/1983 | Wilson |
| 4,409,529 A | 10/1983 | Basford et al. |
| 4,412,454 A | 11/1983 | Yamashita et al. |
| 4,503,705 A | 3/1985 | Polchainoff |

(List continued on next page.)

FOREIGN PATENT DOCUMENTS

| | | | | |
|---|---|---|---|---|
| EP | 136247 | | 3/1985 | |
| GB | 2 013 617 A | * | 8/1979 | .................... 414/5 |
| JP | 2-59290 | * | 2/1990 | .................... 414/5 |
| JP | 2-284888 | * | 11/1990 | .................... 414/5 |
| SU | 166099 | * | 11/1965 | ................... 623/25 |
| SU | 249555 | * | 1/1970 | ................... 623/24 |
| SU | 0584842 | | 7/1977 | |
| SU | 785842 | * | 12/1980 | .................... 414/5 |
| SU | 1627172 A1 | * | 2/1991 | ................... 623/57 |

OTHER PUBLICATIONS

Williams, "Transformers and Optocouplers Implement Isolation Techniques", EDN, 27(2) Jan. 1982.*

Stuart I. Yaniger, 1990, Force and Position Sensing Registors: An Emerging Technology, Interlink Electronics, Capintera, CA, (Apr. 1990).

(List continued on next page.)

Primary Examiner—David H. Willse
(74) Attorney, Agent, or Firm—Michael Best & Friedrich LLP

(57) ABSTRACT

An apparatus for providing a person with stimuli corresponding to an external operation on a sensor of a prosthetic device used in conjunction with a prosthetic or sensory impaired limb. A lower limb prosthesis includes sensors located in a prosthetic foot, contacts in the socket producing stimuli felt on the residual limb, and an electronic unit to adjust and control the magnitude of the stimuli. The sensors are either inductance-based or resistance-based. An upper limb prosthesis comprises a pressure sensor located in the thumb of a prosthetic hand, a vibrating motor generating sensations felt in the residual limb and an electronic circuit to control the vibrating motor and to adjust the intensity of the vibrations. An apparatus for a sensory impaired limb providing a sense of feel to a remote but unimpaired body part are constructed in a similar manner.

53 Claims, 10 Drawing Sheets

U.S. PATENT DOCUMENTS

| | | | |
|---|---|---|---|
| 4,647,918 | A | 3/1987 | Goforth |
| 4,665,753 | A | 5/1987 | Betrand |
| 4,745,930 | A | 5/1988 | Confer |
| 4,760,850 | A | 8/1988 | Phillips et al. |
| 4,770,662 | A | 9/1988 | Giampapa |
| 4,808,187 | A | 2/1989 | Patterson |
| 4,862,743 | A | 9/1989 | Seitz |
| 4,876,758 | A | 10/1989 | Rolloff et al. |
| 4,878,913 | A | 11/1989 | Aebischer et al. |
| 4,896,053 | A | 1/1990 | Kesselring |
| 4,987,783 | A | 1/1991 | D'Antonio et al. |
| 5,033,291 | A | 7/1991 | Podoloff et al. |
| 5,033,999 | A | 7/1991 | Mersky |
| 5,070,737 | A | 12/1991 | Reilly |
| 5,079,949 | A | 1/1992 | Tamori |
| 5,088,503 | A | 2/1992 | Seitz |
| 5,246,463 | A | 9/1993 | Giampapa |
| 5,253,654 | A | 10/1993 | Thomas et al. |
| 5,253,656 | A | 10/1993 | Rincoe et al. |
| 5,255,753 | A | 10/1993 | Nishikawa et al. |
| 5,358,514 | A | 10/1994 | Schulman et al. |
| 5,408,873 | A | 4/1995 | Schmidt et al. |
| 5,413,611 | A | 5/1995 | Haslam, II et al. |
| 5,443,528 | A * | 8/1995 | Allen .......................... 623/52 |
| 5,449,002 | A | 9/1995 | Goldman |

OTHER PUBLICATIONS

Brochure describing Force sensing resistor marketed by Interlink Electronics of Carpinteria, CA.

Endicott Roemer et al., *Leg Load Warning System for the Orthopeadically Handicapped*, MEDICAL AND BIOLIGICAL ENGINEERING, May 1994, Brooks and Meisel, pp. 318–320.

Prior et al., *Supplemental Sensory Feedback for VA/NU Myoelectric Hand*, BULLETIN OF PROSTHETICS RESEARCH, Fall 1976, pp. 170–191.

Miyazaki et al., *Limb–load Alarm Device for Partial Weight–Bearing Walking Exercise*, MEDICAL & BIOLOGICAL ENGINEERING & COMPUTING, Sep. 1978, pp. 500–505.

*A Myoelectrically–Controlled Prosthesis with Sensory Feedback*, MEDICAL & BIOLIGICAL ENGINEERING & COMPUTING, Jan. 1979, pp. 73–80.

Petrofsky et al. *Computer Controlled Walking in the Paralyzed Omdovodia*, THE JOURNAL OF NEUROLOGICAL AND ORTHOPEDIC SURGERY, vol. 4, 1983, pp. 153–164.

Beeker et al., *Artificial Touch in a Hand–Prosthesis*, MEDICAL & BIOLOGICAL ENGINEERING, vol. 5, 1967, pp. 47–49.

Spolek et al., *An Instrumented Shoe –A Portable Force Measuring Device*, JOURNAL OF BIOMECHANICS, vol. 9, 1976, pp. 779–783.

Saxema et al., *EMG Operated Electronic Artificial Leg Controller*, 15 MEDICAL & BIOLOGICAL ENGINEERING & COMPUTING, vol. 15, 1977, pp. 553–557.

* cited by examiner

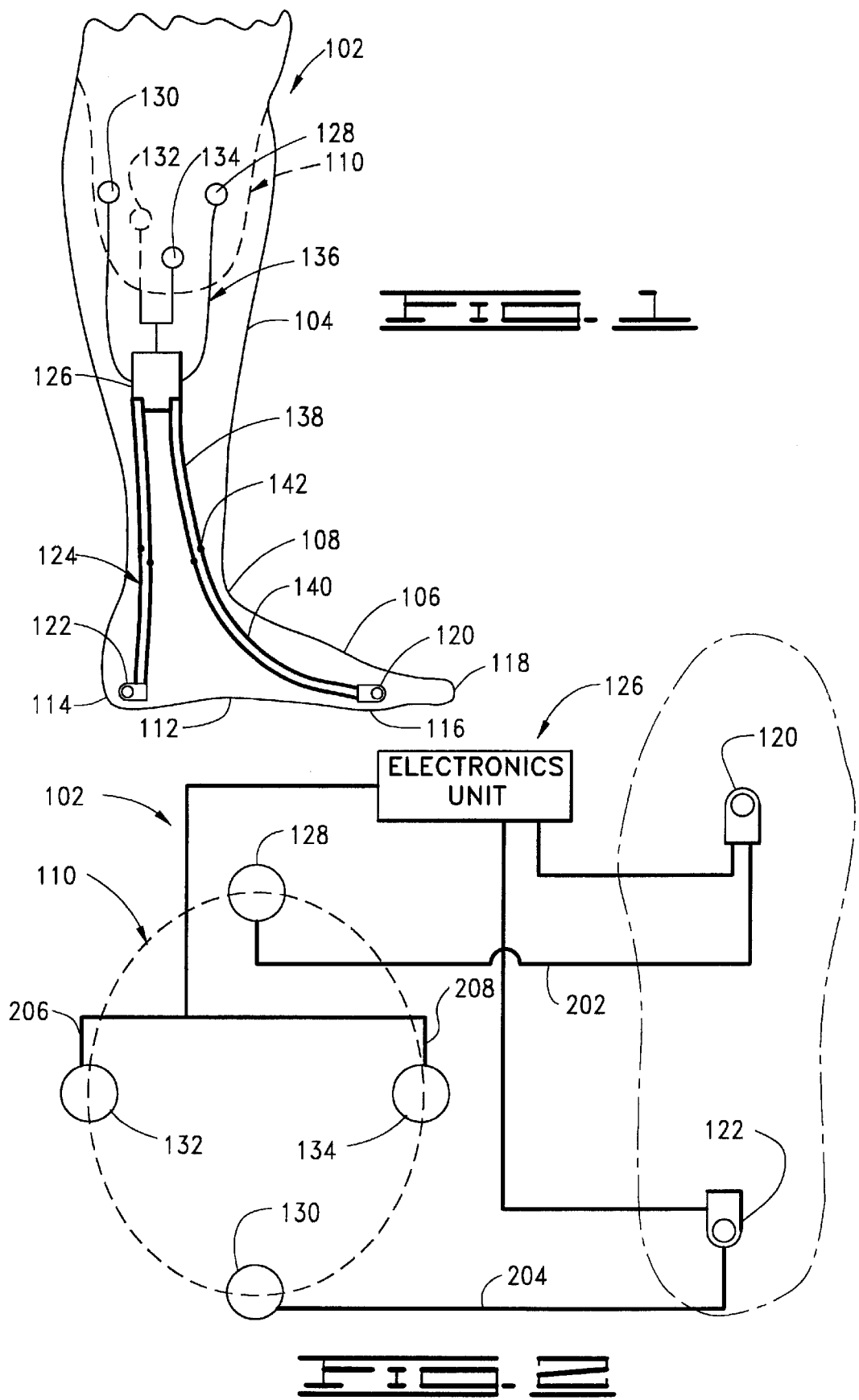

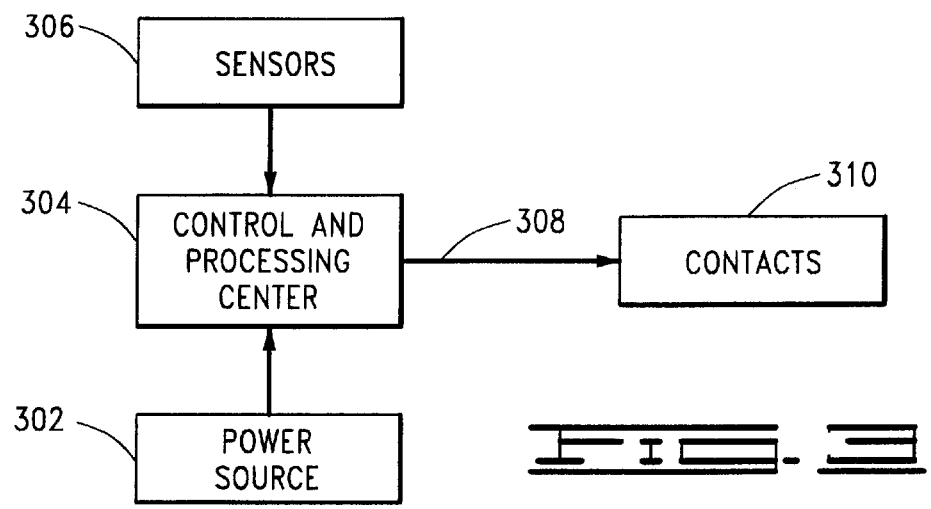
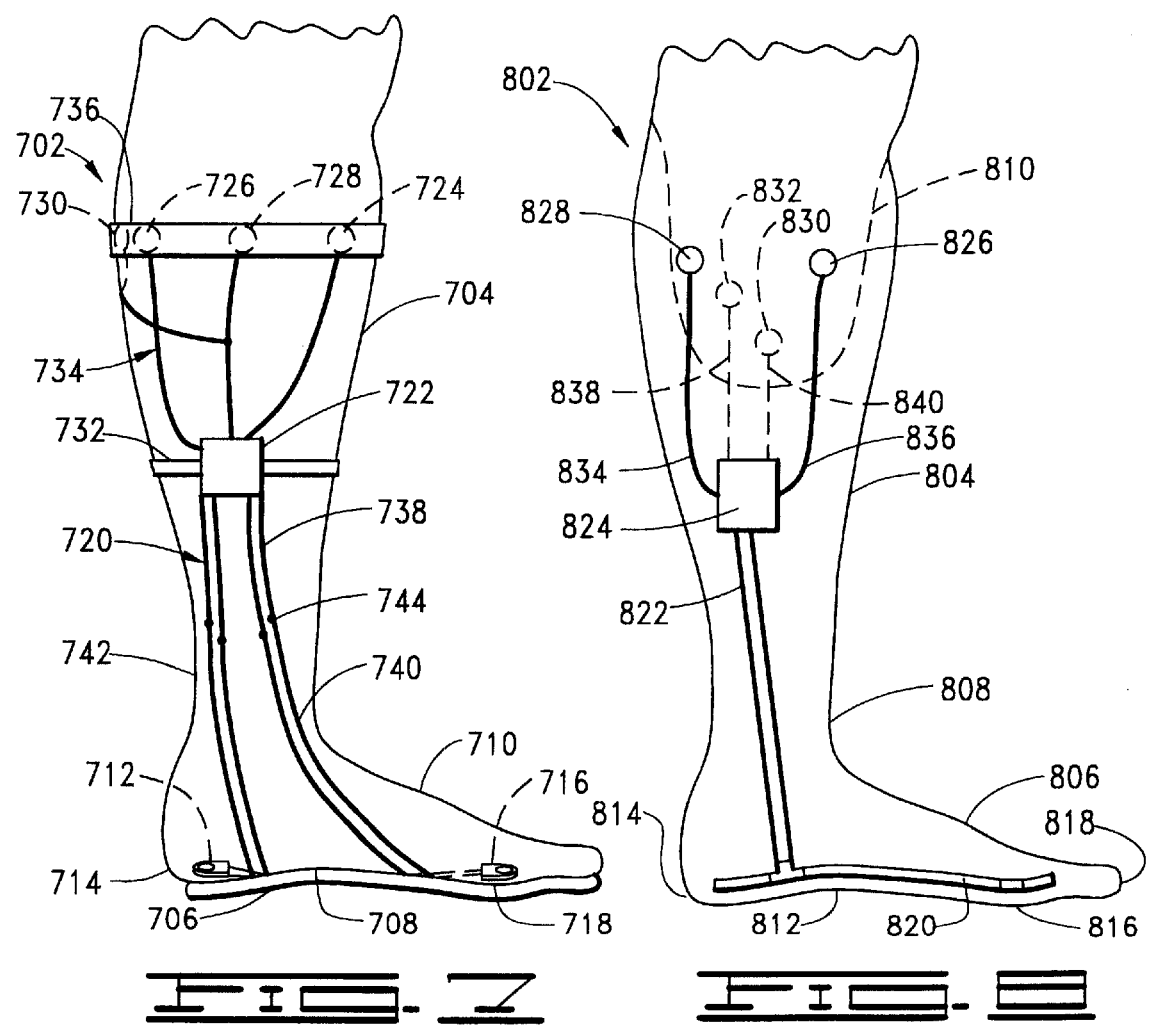

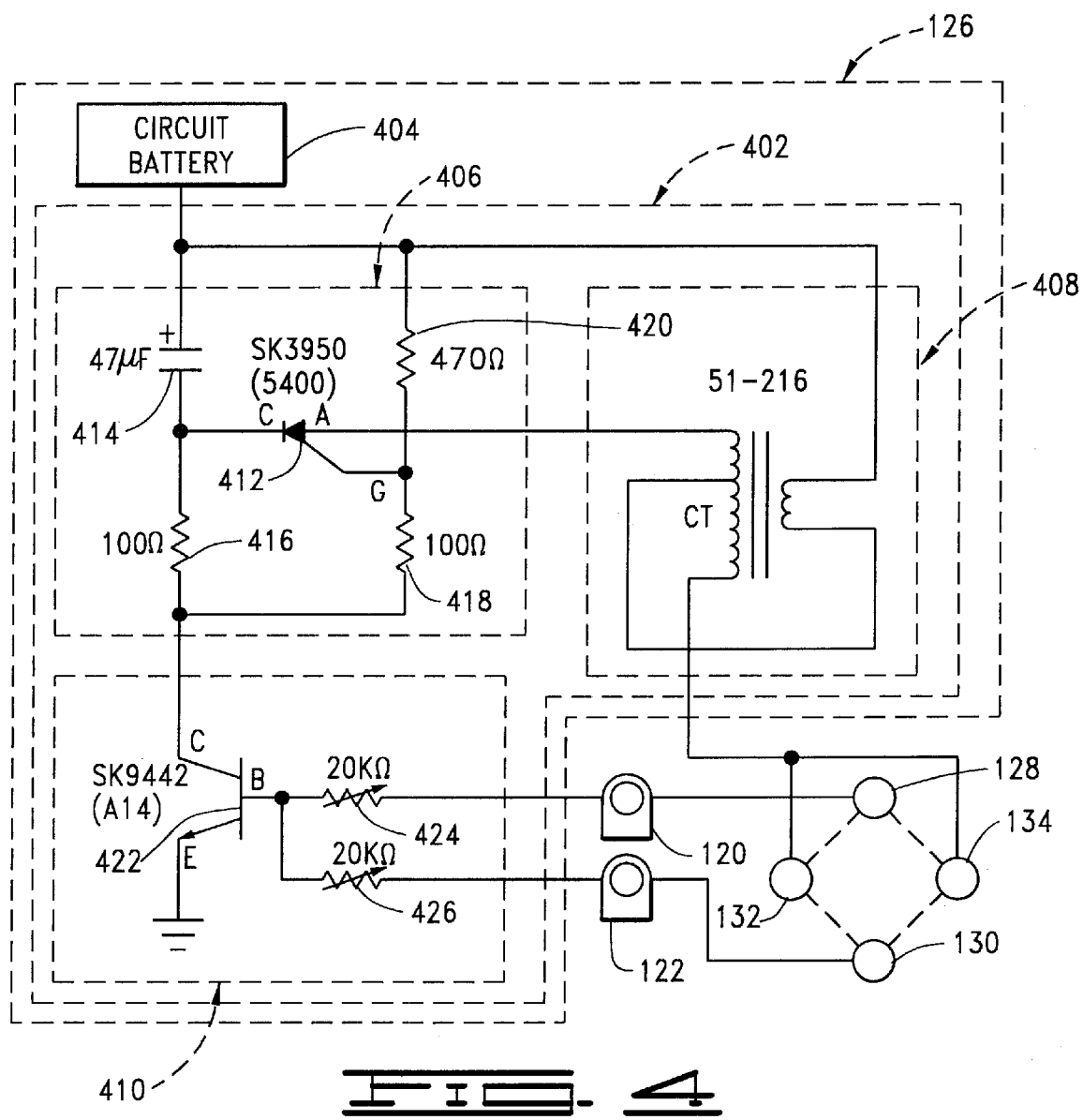
FIG. 4
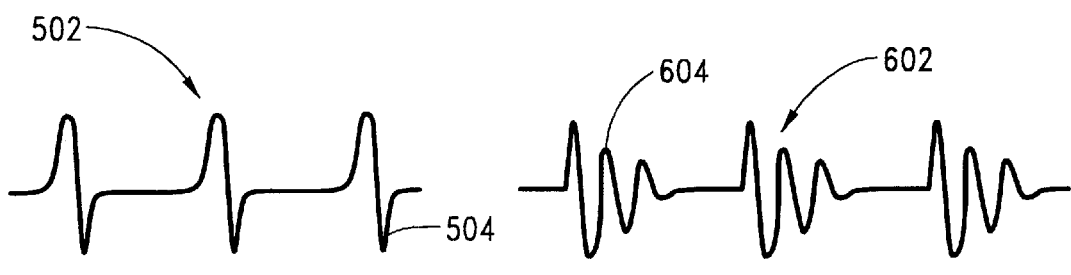
FIG. 5
FIG. 6

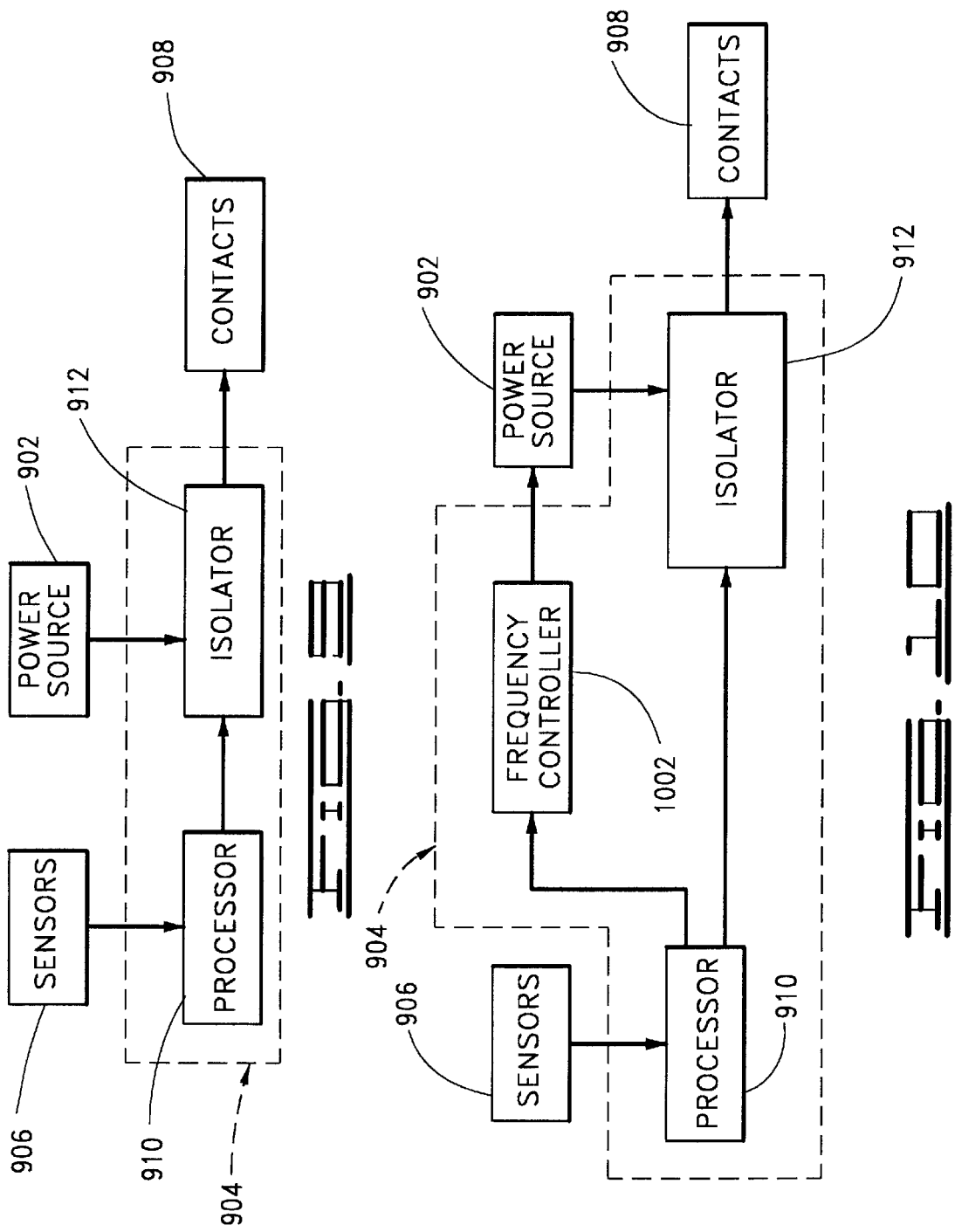

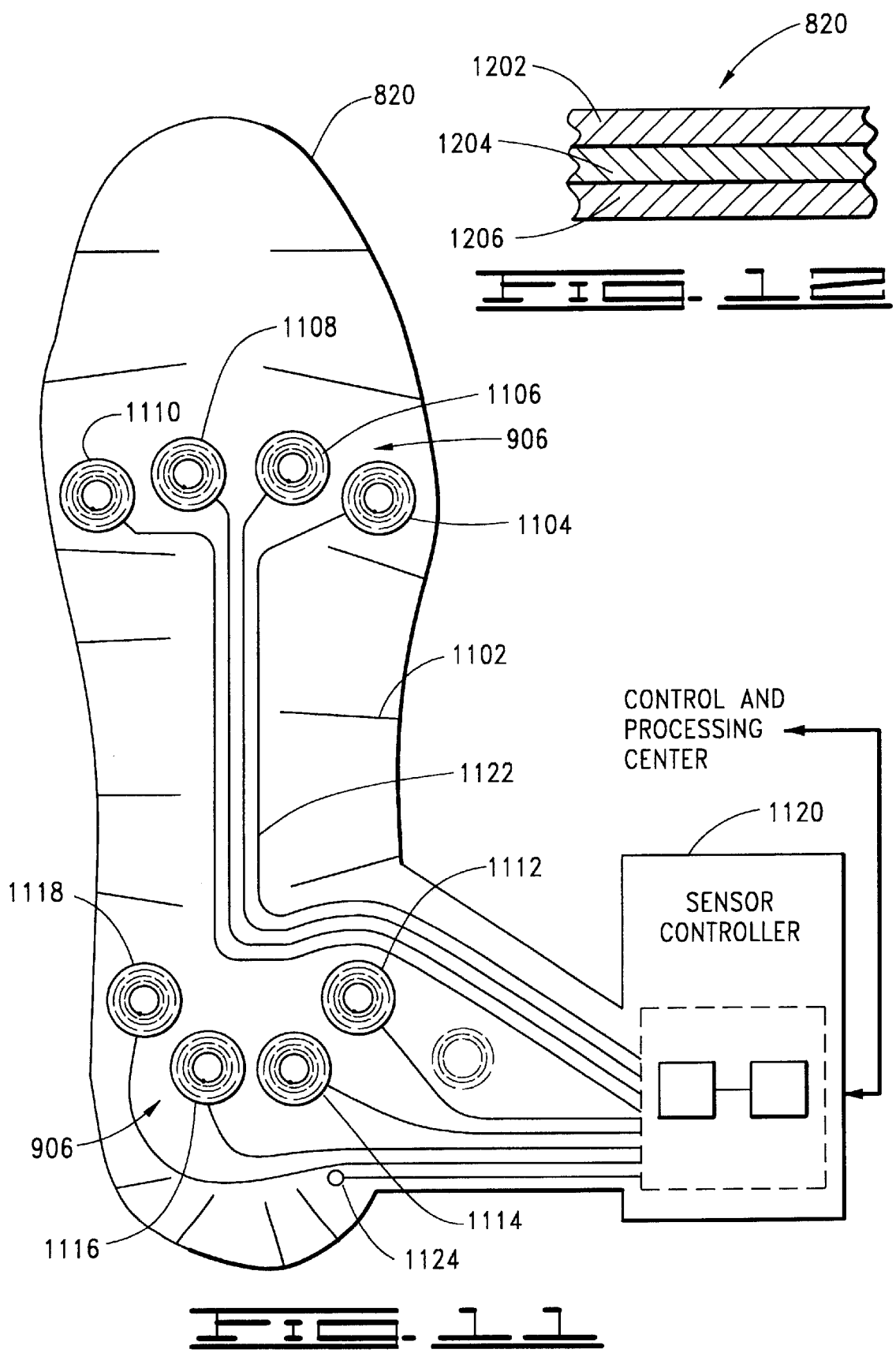

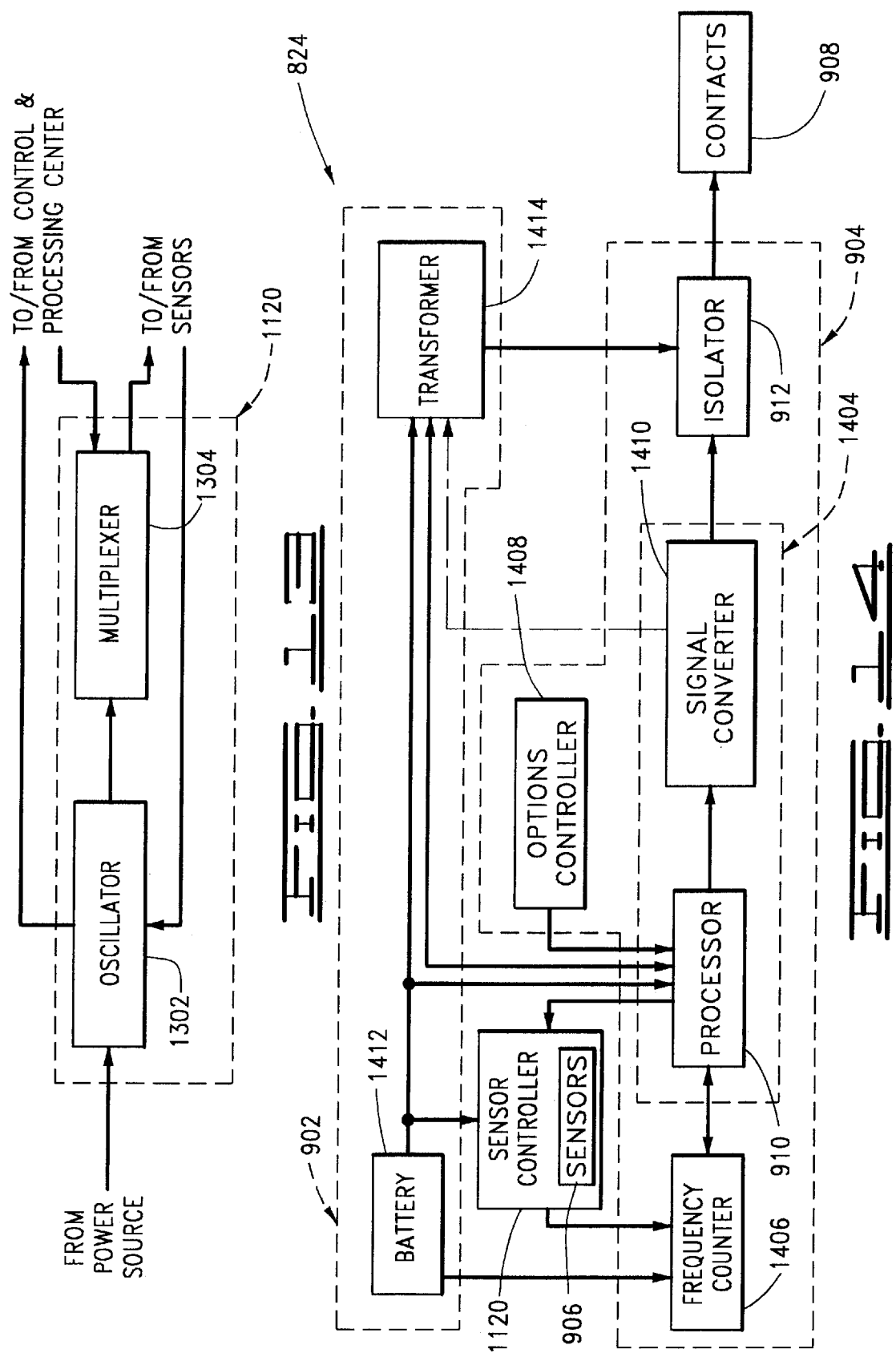

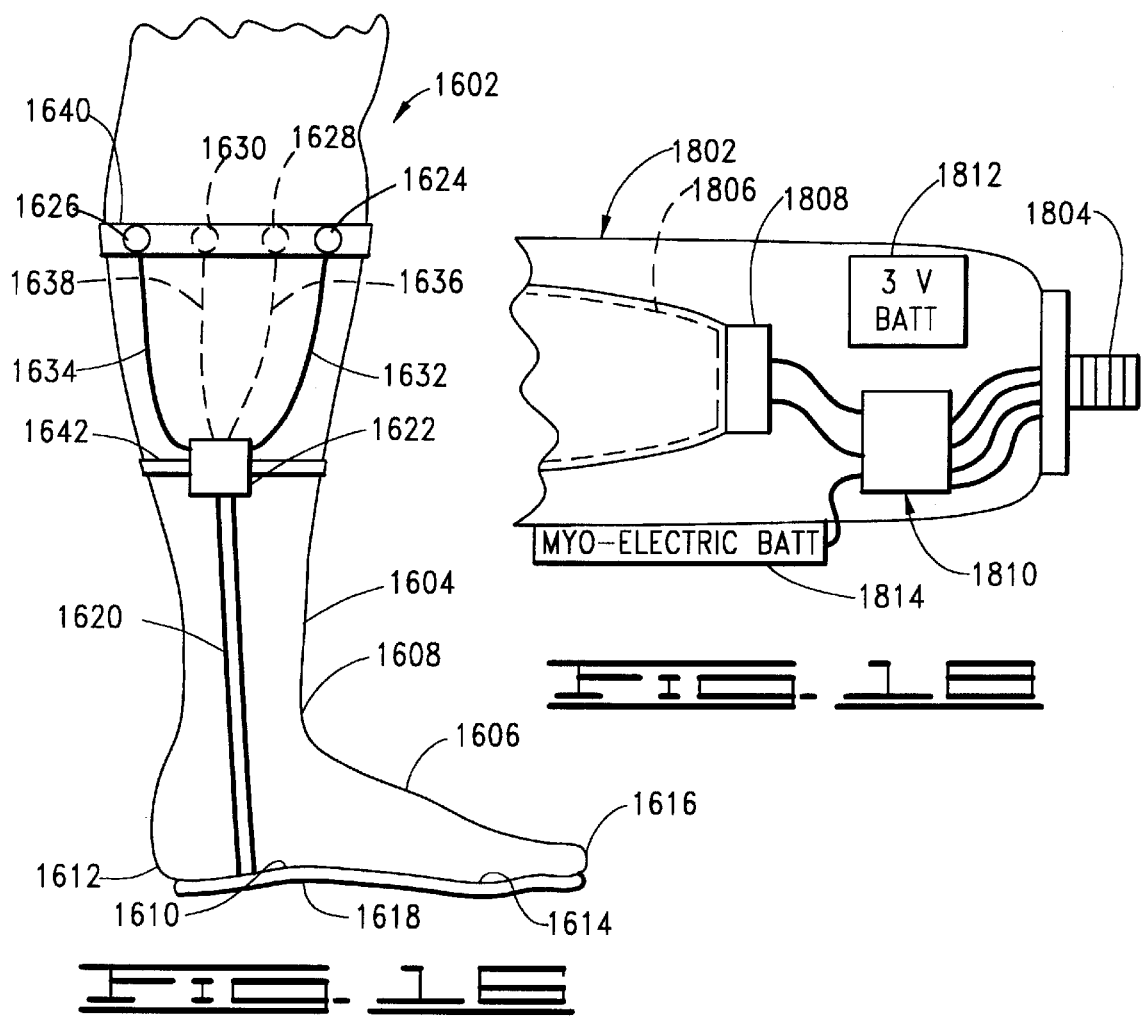
FIG. 18
FIG. 16
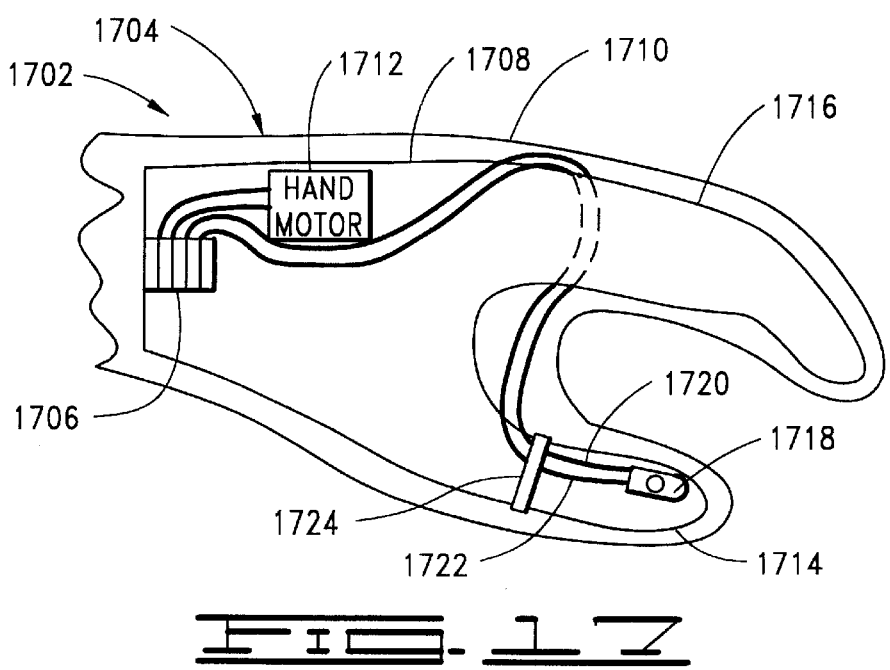
FIG. 17

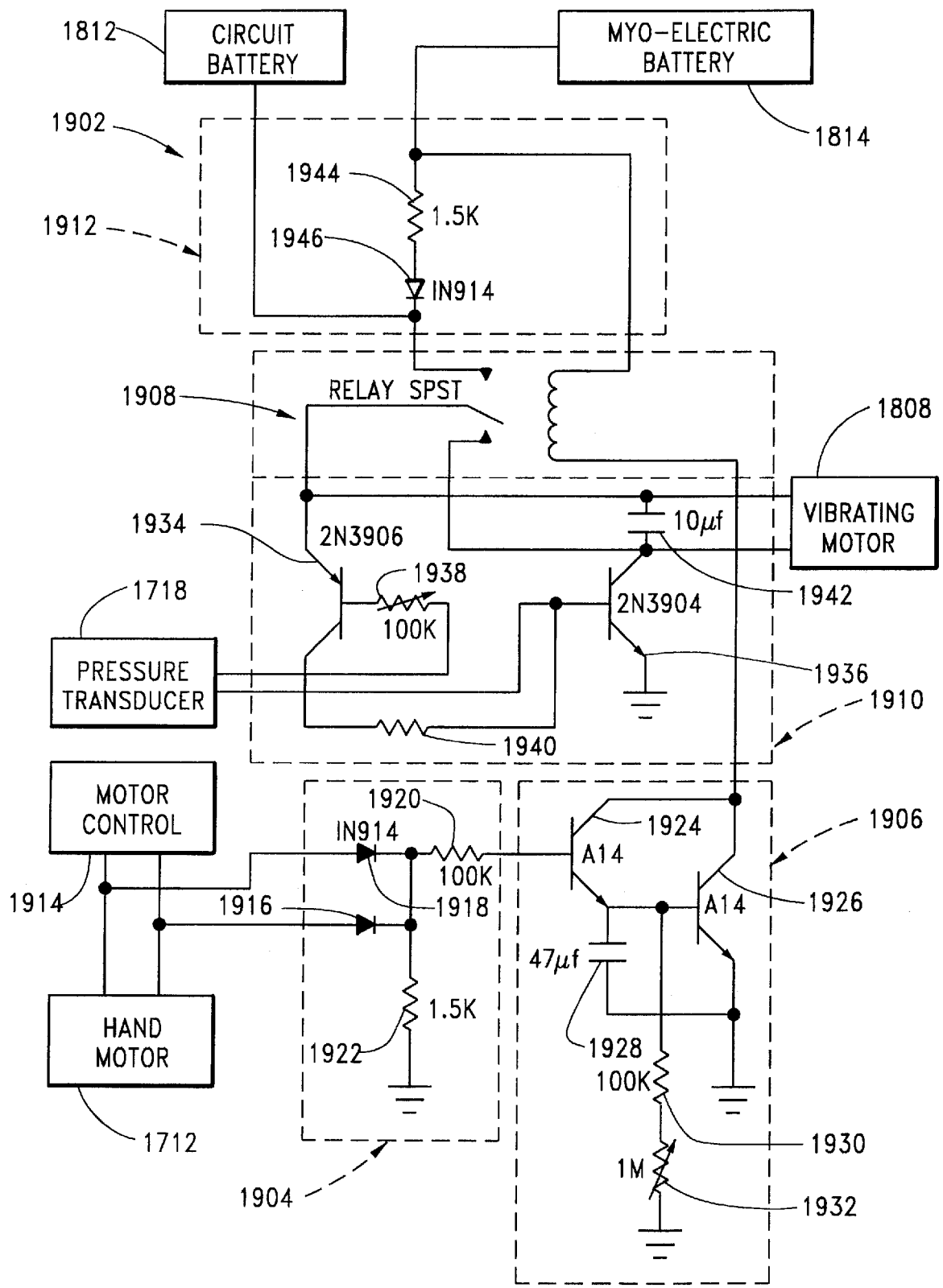

SYSTEM AND METHOD FOR PROVIDING A SENSE OF FEEL IN A PROSTHETIC OR SENSORY IMPAIRED LIMB

This is a continuation-in-part of application Ser. No. 08/281,491 filed on Jul. 27, 1994, now abandoned, which was a continuation of application Ser. No. 07/942,205 filed on Sep. 8, 1992, now abandoned.

FIELD OF THE INVENTION

The present invention relates to devices for providing a person with a sense of feel in a prosthetic or sensory impaired limb.

SUMMARY OF THE INVENTION

The present invention is directed to a method for providing sensory perceptions in a sensor system of a prosthetic device. The method comprises sensing an external operation magnitude from a plurality of sensor groups, each sensor group sensing a fraction of the external operation magnitude. A plurality of sensory inputs from the sensor groups is generated in response to the external operation. An electrical input signal with a magnitude also is generated. The electrical input signal is controlled with the plurality of sensory inputs to create a plurality of sensory output signals collectively having a stimulus with a collective stimulus magnitude corresponding to the electrical input signal magnitude. Each sensory output signal has a fraction of the stimulus magnitude corresponding to the fraction of the external operation magnitude sensed by one of the sensor groups. Each of the sensory output signals is transmitted to a designated one of a plurality of contacts through a designated one of a plurality of channels.

Still further, the present invention comprises a sensory feedback system for use with a prosthetic device. The sensory feedback system comprises a power source that is adapted to transmit an electrical input signal. Included are a plurality of sensors each operable to create a sensory inputs in response to an external operation thereon. Further, the sensory feedback system comprises a plurality of contacts each adapted to receive a sensory output signal. The sensory feedback system includes a plurality of channels each connected to one of the plurality of contacts and adapted to carry one of the sensory output signals to the contact to which it is connected. The sensory feedback system also comprises a control and processing center adapted to receive the electrical input signal from the power source and to receive the sensory inputs from the pressure sensors, to control the electrical input signal by applying the sensory inputs to the electrical input signal to create the sensory output signals, and to transmit the sensory output signals to the contacts through the channels.

Further still, the present invention comprises a sensory feedback system for a prosthetic device. The sensory feedback system comprises a power source adapted to transmit an electrical power signal and an electrical input signal, a control and processing center adapted to receive the electrical input signal and to transmit a plurality of sensory output signals, and a plurality of contacts each adapted to receive a designated one of the sensory output signals. The sensory feedback system also comprises a plurality of inductance-based pressure sensors each adapted to receive the electrical power signal, to change the electrical power signal to a sensory input signal representing pressure applied thereto, and to transmit the sensory output signal therefrom. Also comprising the sensory feedback system is a sensor controller adapted to route the electrical power signal to each inductance-based pressure sensor and to return the sensory input signal from each inductance-based pressure sensor to the control and processing center. The control and processing center processes the sensory input signals and the electrical input signal to create a plurality of sensory output signals each representing the pressure applied to at least one of the inductance-based pressure sensors. In addition, the control and processing center transmits the sensory output signals to the contacts.

In another aspect, the present invention is directed to a lower limb prosthesis. The lower limb prosthesis includes a leg portion including a socket for receiving a residual limb of an amputee. A foot portion is attached to the leg portion. The foot portion having a sole, and a pressure sensor is positioned under the sole of the foot to provide an electrical resistance in proportional response to pressure against the sole of the foot. A power source is included to generate an electrical power signal, and an electrical power signal conductor is included to conduct the electrical power signal from the power source to the pressure sensor. A control and processing center also is included. The control and processing center is adapted to respond to the electrical resistance in the pressure sensor, whereby the power source is deactivated in response to electrical resistance in the pressure sensor which is greater than a selected level of electrical resistance and whereby the power source is activated in response to electrical resistance in the pressure sensor which is less than the selected level of resistance. A residual limb contact is included to transmit the electrical power signal to the residual limb. In addition, a channel is included to conduct a sensory output signal from the pressure sensor to the residual limb contact.

In yet another aspect, the present invention is directed to a lower prosthesis. The lower limb prosthesis comprises a leg portion including a socket for receiving the residual limb of an amputee. A foot portion is attached to the leg portion, the foot portion having a sole with a heel and a ball of the foot. A first pressure sensor is position under the ball of the foot adapted to provide an electrical resistance in proportion to pressure against the ball of the foot with respect to total pressure, and a second pressure sensor is positioned under the heel adapted to provide an electrical resistance in proportion to pressure against the heel with respect to total pressure. A power source is included to generate electrical current having a magnitude. An electrical current conductor is included to conduct electrical current from the power source to the first and second pressure sensors.

The lower limb prosthesis further comprises a first residual limb contact adapted to transmit electrical to a first location on the residual limb. A first channel conducts electrical current from the first pressure sensor to the first residual limb contact. A second residual limb contact is included to transmit electrical to a second location on the residual limb. A second channel conducts electrical current from the second pressure sensor to the second residual limb contact. The lower limb prosthesis further comprises a control and processing assembly adapted to create a first and second sensory output signal collectively having a stimulus with a collective stimulus magnitude corresponding to the electrical current magnitude. Each sensory output signal has a fraction of the stimulus magnitude corresponding to the fraction of the pressure sensed by the respective sensors with respect to the total pressure.

In still another aspect, the present invention comprises an upper limb prosthesis. The upper limb prosthesis includes an arm portion including a socket adapted to receive the residual limb of the amputee. A hand portion is attached to the arm portion, the hand portion having at least one digit. A power source generates an electrical current. A pressure sensor is installed in the at least one digit to receive the electrical current, to provide an electrical resistance to pressure on the at least one digit, and to emit, in response to the pressure, an electrical signal in proportion to the intensity of pressure on the at least one digit.

The upper limb prosthesis further comprises a control and processing center adapted to convert the electrical signal from the pressure sensor to a stimulus, to deactivate the transmission of the stimulus to the residual limb in response to a predetermined period of lack of muscle activity in the residual limb, and to activate the transmission of the stimulus in response to muscle activity in the residual limb. A residual limb contact is provided to receive the stimulus from the control and processing center and to transmit the stimulus to the residual limb.

The present invention is also directed to a system for providing sensory feedback to a person having a prosthetic device The system comprises a plurality of sensors. Each of the sensors is located at a respective area of the prosthetic device and has a sensor characteristic to define a plurality of sensor characteristics. Each of the sensor characteristics indicates a degree of exposure of the respective sensor to an external influence. The sensor characteristic of each of the sensors defines a sensor fraction of the total of the sensor characteristics.

The system further comprises a plurality of output elements, each of the output elements corresponding to one of the sensors and being in communication with a sensory-perceptive area of the person. The system also includes a control and processing center operatively connected to the sensors and to the output elements. The control and processing center produces a sensory output in each of the output elements to define a plurality of sensory outputs. The sensory output of each of the output elements defines an output fraction of the total of the sensory outputs. The output fraction is substantially equal to the sensor fraction of the corresponding sensor.

DESCRIPTION OF THE DRAWINGS

FIG. 1 is a diagrammatic view of an apparatus constructed in accordance with the present invention for use with a lower limb prosthesis.

FIG. 2 is a diagram illustrating the location of the sensors, the electronic circuit, and the contacts in the apparatus of FIG. 1.

FIG. 3 is a block diagram of the processing in the electronic circuit of the apparatus of FIG. 1.

FIG. 4 is an electrical schematic of the electronic circuit of the apparatus of FIG. 1.

FIG. 5 is a graph illustrating the waveform of a prior art pulsating unit.

FIG. 6 is a graph illustrating the waveform of the pulses of the electronic circuit of FIG. 4.

FIG. 7 is a diagrammatic view of an apparatus constructed in accordance with the present invention for use with a natural lower limb which is sensory impaired.

FIG. 8 is a diagrammatic view of a digital processing apparatus constructed in accordance with the present invention for use with a lower limb prosthesis.

FIG. 9 is a block diagram of the processing in the electronic circuit of the apparatus of FIG. 8.

FIG. 10 is a block diagram of the frequency control processing in the electronic circuit of the apparatus of FIG. 8.

FIG. 11 is a diagram illustrating the sensor unit of the apparatus of FIG. 8.

FIG. 12 is a cross sectional view of the sensor unit of FIG. 11.

FIG. 13 is a block diagram of the sensor controller of FIG. 11.

FIG. 14 is a block diagram of the electronic circuit of the apparatus of FIG. 8.

FIG. 16 is a diagrammatic view of a digital processing apparatus constructed in accordance with the present invention for use with a natural lower limb which is sensory impaired.

FIG. 17 is a diagrammatic view of the hand component of an apparatus constructed in accordance with the present invention for an upper limb prosthesis.

FIG. 18 is a diagrammatic view of a socket component of an apparatus constructed in accordance with the present invention for an upper limb prosthesis.

FIG. 19 is an electrical schematic of the electronic circuit of the upper limb prosthesis shown in FIGS. 17 and 18.

DETAILED DESCRIPTION OF THE PREFERRED EMBODIMENTS

Figure 15:
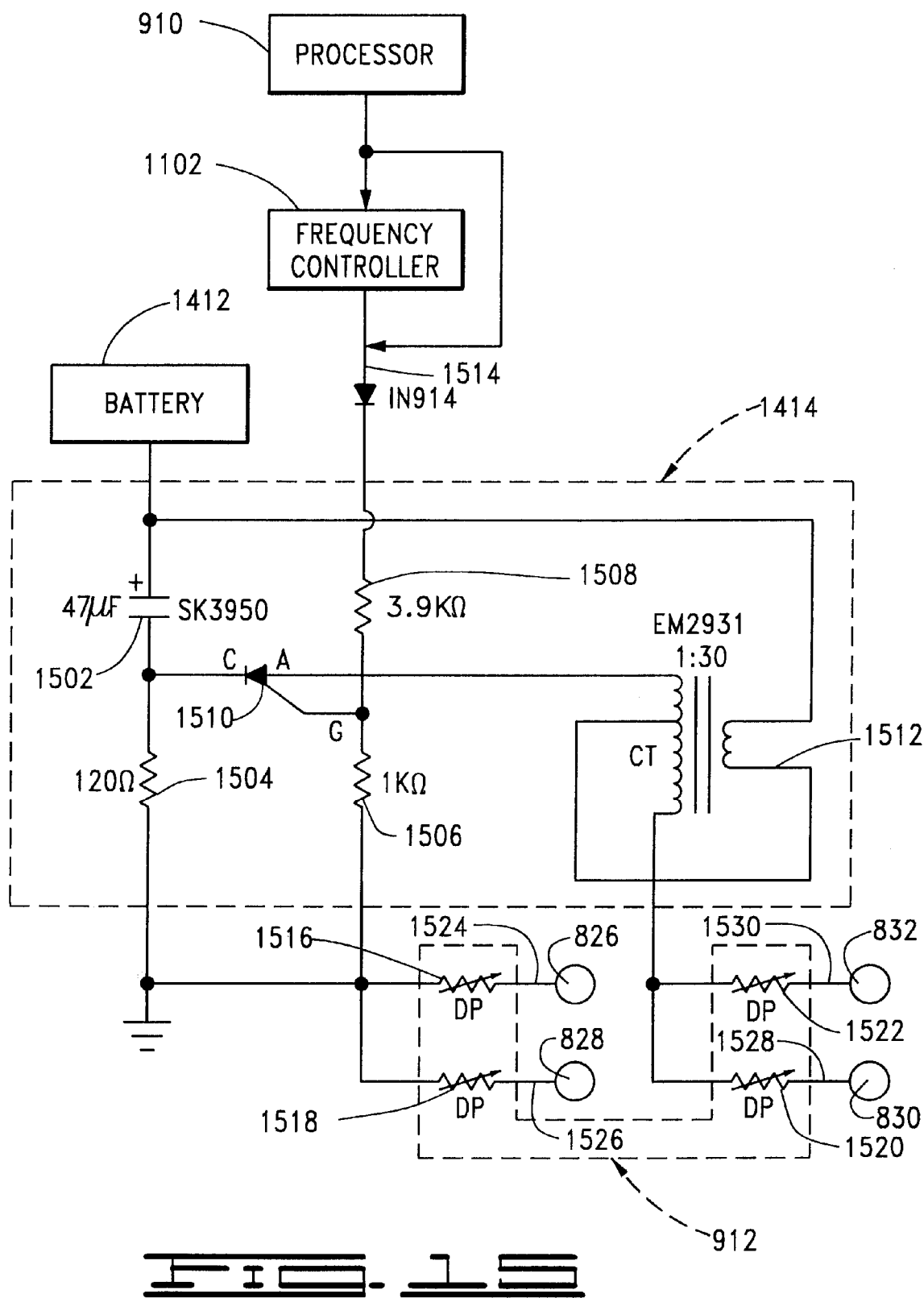
FIG. 15 is an electrical schematic of the electronic circuit of the apparatus of FIG. 8.

A person with a prosthetic limb or a sensory impaired limb faces a challenging task in coordinating the use of such a limb. Without sensory information from a lower extremity to the brain, there is no feedback to the individual indicating how much pressure is being placed on a particular area of the limb. When the brain receives no sensory perception from an upper extremity limb, an object may be grasped too loosely and dropped or squeezed too tightly and damaged. Moreover, without feedback to the brain of other stimuli, such as heat or cold, a prosthetic limb or sensory impaired limb may be damaged.

In the case of the lower extremities in particular, the loss of feeling contact with the floor or ground presents difficulty in maintaining proper balance, in achieving a normal gait, and in being aware of prolonged or excessive contact with the ground or floor. In conventional lower limb prostheses, the amputee usually can feel pressure from the socket on the residual limb. However, the pressure sensations are so generalized that the amputee cannot distinguish the position of the foot or the limb from the pressure sensations. Lack of balance and an abnormal gait may result in a fall and serious injury.

In a natural but sensory impaired limb, prolonged or excessive pressure can cause ulceration and infections. These ulcers, also called pressure sores, require extended medical treatment and, in extreme cases, can even lead to amputation.

The present invention provides a sense of feel in a prosthetic device by producing sensory data to a person at remote points on the body. As used herein, the term "prosthetic device" means a prosthetic limb, a device used in conjunction with a sensory impaired limb or sensory impaired body part, or any other device used to provide sensory information to a person or to replace a missing part of a person's body.

In one aspect, for example, stimuli which are proportional to pressure exerted on locations on the limb are produced on parts of the body so that specific pressure points may be identified. These stimuli are communicated to the brain through the neurological system. When receiving sensory data associated with a missing or impaired limb, the brain may actually project the limb back into the mind through a phenomenon called "cerebral projection." Balance and feeling are not only improved, but a sense of reconnection and movement of the limb may be produced. The sense of reattachment, in turn, may reduce or eliminate phantom pain which often results from a missing or sensory deprived limb.

The Embodiment of FIGS. 1–6

Referring now to the drawings in detail, and to FIG. 1 in particular, shown therein and designated by the reference numeral 102 is a first embodiment of an apparatus constructed in accordance with the present invention. In this embodiment, the apparatus is adapted for use with a lower limb prosthesis 104 which is worn on the residual limb (not shown) of an amputee.

The lower limb prosthesis 104 has a foot portion 106, an ankle portion 108, and a socket portion 110 (shown in broken lines). The socket portion 110 receives the residual limb of the amputee. The foot portion 106 includes a sole 112, a heel 114, a ball of the foot 116, and a toe 118.

Sensor groups which sense an external operation thereon are integrated in, or attached to, the prosthesis 104. A front sensor group, such as a front pressure sensor 120, is located in the sole 112 in the ball of the foot 116. A back sensor group, such as a back pressure sensor 122, is located in the sole 112 toward the heel 114 of the foot 106. Each of the sensors 120 and 122 have a sensor characteristic that describes what electrical characteristic the sensors use to sense the external operation thereon. The sensor characteristic can be, for example, inductance, resistance, impedance, or another characteristic. The pressure sensors 120 and 122 are connected by wiring 124 to an electronics unit 126.

The electronics unit 126 comprises an electronic circuit, yet to be described, contained within an enclosure of some sort. The electronics unit 126 is strapped or otherwise attached to the lower limb prosthesis 104 where it is accessible for adjustment and repair.

Referring still to FIG. 1 and now also to FIG. 2, the apparatus 102 also includes output elements, such as four contacts 128, 130, 132, and 134, which are positioned in the socket portion 110 of the prosthesis 104. A front contact 128 is positioned so as to contact the front of the residual limb, and a back contact 130 is located to be in contact with the back of the residual limb. The other two contacts 132 and 134 are common contacts and are positioned to contact opposing sides of the residual limb of the amputee.

The left and right common contacts 132 and 134 are floating ground contacts, and the front and back contacts 128 and 130 are non-floating ground contacts. Because the common contacts 132 and 134 are floating ground contacts, a potential difference is created between the front contact 128 and the left common contact 132 or between the back contact 130 and the right common contact 132, respectively. A potential difference occurs when the electric charge at one point in the circuit is not the same as the electric charge at another point in the circuit. This potential difference allows the current to flow through the residual limb from the more positive contact to the more negative contact, thereby completing the circuit path.

As best seen in FIG. 2, the contacts 128, 130, 132, and 134 are connected by channels, such as wiring 136, to the electronics unit 126. The wiring 136 for each channel 202, 204, 206, and 208 connects to each contact 128, 130, 132, and 134, respectively. The wiring 136 completes an electric circuit path from the electronics unit 126 to the front and back contacts 128 and 130, through the residual limb to the common contacts 132 and 134, and back to the electronics unit 126.

Electrode pads which are commonly used for monitoring heart rates and for producing electrocardiograms are suitable for use as the four contacts 128, 130, 132, and 134. The adhesive portions of these monitoring pads may be removed and the elastomeric contact portions of the pads may be secured in the prosthetic limb. As shown in FIG. 1, the contacts 128, 130, 132, and 134 should be positioned within the socket portion 110 so that, when the residual limb is received in the socket of the prosthesis 104, the contacts will firmly contact the surface of the residual limb creating a potential electrical path therethrough.

FIG. 3 illustrates the processing that occurs in the electronics unit 126 of the apparatus 102. (See FIG. 1.) A power source 302 in the electronics unit 126 transmits an electrical input signal to the control and processing center 304. In the apparatus 102 of the present invention, the electrical input signal has a voltage and a current, each with a magnitude, with a circuit path is closed.

When an external operation, such as pressure, is applied to the sensors 306, the sensors input sensory input to be processed by the control and processing center 304. In the apparatus 102 of the present system, the sensory input is a resistance value.

The control and processing center 304 applies the sensory inputs to the electrical input signal to control the output of the electrical input signal. The output is carried as sensory output signals on separate channels 308 to one or more contacts 310. Each of the sensory output signals represent a stimulus with a stimulus magnitude. The stimulus can be, for example, a pulsating current having a current magnitude and a frequency.

Because the sensory input signals are first processed and then used to control the output of the electrical input signal, multiple sensory output signals can be carried on a different one of the multiple channels 308 to a designated one of the contacts 310. Each sensory output signal carries a fraction of the total sensory output. Thus, for example, the front contact 128 can receive a different pulsating current than the back contact 130. (See FIG. 1.)

The processing in the apparatus 102 is analogous to a water faucet system. The electrical input signal is analogous to water in the pipes of the water faucet system. The contacts are analogous to the faucets. The processed sensory input signals that are applied to the electrical input signal to control the sensory output signals sent to each individual contact are each analogous to a signal that is transmitted to a different faucet to allow the water to come out of each individual faucet at a different pressure and rate.

With reference now to FIG. 4, the electronic circuit 402 contained within the electronics unit 126 of the apparatus 102 is described in detail. The electronic circuit 402 is an analog control and processing center 304 (see FIG. 3). The electronic circuit 402 is powered by a power source, such as a circuit battery 404. Current from the battery 404 is transformed into oscillations or pulses by an oscillator circuit 406 which drives the transformer 408. The pulses are damped by a trigger circuit 410 which also controls the amplitude of the pulses.

In the preferred practice, the circuit battery 404 is a standard nine-volt d.c. battery. A Heath No. 51-216 step-up transformer or an equivalent is a suitable driver transformer 408. The oscillator circuit 406 includes an SK3950 (5400) SCR transistor 412, a 47 µf chip capacitor 414, and resistors 416, 418 and 420.

The trigger circuit 410, which receives the pulses from the oscillator circuit 406, includes an SK9442 (A14) transistor 422. The trigger input from the SK9442 transistor 422 is connected to front and back 20 kilo-ohm (KΩ) potentiometers 424 and 426, respectively.

The potentiometers 424 and 426 are included to allow the amputee to adjust the magnitude of the stimuli produced in the sensory output signals transmitted to the contacts 128, 30, 132, and 134. The potentiometers 424 and 426 may be standard variable resistors in the range of 20 KΩ to 150 KΩ, depending upon the desired range of magnitudes.

With continuing reference to FIG. 4, the front potentiometer 424 is in series with the front pressure sensor 120 and the front contact 128. Pulses of current are generated as the electrical input signal by the battery 404 of the electronics unit 126 and are directed to the pressure sensor 120. The resistances from the pressure sensors 120 act as the sensory inputs which are used to process the electrical input signal to create the sensory output signals. When sufficient pressure is exerted on the pressure sensor 120 to reduce the resistance, the current pulses of the electrical input signal are changed to current pulses of the sensory output signal which flow to the contact 128. As the resistance of the pressure sensors 120 change, the current pulses of the sensory output signals change. This series arrangement forms a front potentiometer/sensor set.

Similarly, the back potentiometer 426 is in series with the back sensor 122 from which the current pulses of the sensory output signals are transmitted to the back contact 130, assuming reduced resistance resulting from pressure. Thus, there is provided a back potentiometer/sensor set, which is in parallel arrangement with the front potentiometer/sensor set.

Voltage initiated by the driver transformer 408 as the electrical input signal is changed to current and directed to the contacts 128 and 130 as the sensory output signals and is transceived through the front and back contacts 128 and 130. The current is also transceived through the flesh of the residual limb (not shown in FIG. 4) through the common contacts 132 and 134, as described above.

As indicated, the resistance in the pressure sensors 120 and 122 is the sensory input that controls the stimuli perceived by the amputee relative to the degree of pressure exerted on the pressure sensors. To this end, the pressure sensors 120 and 122 have a range of resistance from ∞ KΩ, when no pressure is applied, to approximately 10 KΩ, when extreme pressure is applied. The DYNAFORCE pressure sensor manufactured by TekScan, Inc. in Boston, Mass., the FORCE SENSING RESISTOR™ manufactured by Interlink Electronics, Inc. in Carpintera, Calif., or an equivalent, are suitable devices for the pressure sensors 120 and 122 in the apparatus 102.

Referring still to FIG. 4, when no pressure is applied to the pressure sensors 120 and 122, the virtually infinite resistance of the pressure sensors results in an open circuit and no current flows to the contacts 128 and 130. In fact, until pressure is applied to the pressure sensors 120 and 122 to effect a resistance of about one Mega-ohm (MΩ) for one of the potentiometer/sensor sets, the trigger circuit 410 is turned off by the SK9442 transistor 422, thereby deactivating the electronics unit 126. This conserves battery power during periods when no pressure is exerted on the sensors 120 and 122.

When sufficient pressure is applied to produce a resistance in one of the potentiometer/sensor sets which is greater than 200 KΩ but less than 1 MΩ, the trigger circuit 410 will be turned on by the SK9442 transistor 422, activating the electronics unit 126, and current will flow to the contacts 128 and 130. However, in this range the current pulses of the sensory input signal will be insufficient to produce a perceptible stimulus in the residual limb. When sufficient pressure is applied to produce a resistance in one of the potentiometer/sensor sets of approximately 200 KΩ or less, the current pulses to the contacts 128 and 130 are adequate to produce stimuli which can be felt by the amputee.

Now it will be understood that the magnitude of the stimulus transmitted to the residual limb is directly proportional to the amount of pressure applied to the pressure sensors 120 and 122. Increasing the pressure on the sensors 120 and 122 reduces the effective resistance applied to the trigger circuit 410 output and increases the magnitude of the current pulses to the contacts 128 and 130. Likewise, decreasing the pressure on the sensors 120 and 122 decreases or eliminates the magnitude of the current pulses to the contacts 128 and 130.

Patients vary in their sensitivity to electrical current magnitudes. The magnitude of the current that is transmitted to the contacts 128 and 130 can be regulated to a comfortable range for a particular patient by adjusting the potentiometers 424 and 426, as indicated.

When sufficient pressure is applied to the sensors 120 and 122 at the same time, as is the case when the amputee is standing flat-footed, both contacts 128 and 130 produce a stimulus. If each contact 128 and 130 produces stimulus with the same magnitude as it would if acting alone, the amputee would feel the overall effect of doubled magnitude. Over a period of time, this doubled magnitude might become irksome and uncomfortable to the amputee.

This problem is eliminated in the apparatus of the present invention. Because the sensors 120 and 122 are connected in a parallel arrangement, a differential effect is produced when pressure is applied to both sensors 120 and 122 simultaneously. For example, if equal pressure is applied to both sensors 120 and 122 (and the two potentiometers 424 and 426 are adjusted to be equal in resistance), one-half of the output current from the SK9442 transistor 422 flows to the front contact 128 and one-half flows to the back contact 130. When sufficient pressure is applied to both sensors 120 and 122 simultaneously, the amputee feels stimulus from both contacts 128 and 130. However, the collective magnitude of the output current is divided between the two contacts 128 and 130. Therefore, the collective magnitude of the stimulus felt by the person from the contacts 128 and 130 is lessened.

In addition, the collective magnitude intensity is divided with respect to an absolute reference. Thus, the collective magnitude of the current is allocated at one-hundred percent of the total magnitude from the zero output level. Other systems use a floating reference that jumps to the one-hundred percent level when force is applied, but then stabilize to zero when the pressure no longer increases, even though force is still applied. Then, when the force is released, the floating reference jumps to a negative one-hundred percent magnitude and then stabilizes to zero. Thus, the absolute reference used by the current system provides a higher comfort level.

With reference now to FIG. 5, a typical waveform 502 produced by a conventional electrical stimulus unit is described. It is important to note the sharp lower peaks, one of which is designated by reference numeral 504, caused by the recoil of driver transformer windings. Over time, these sharp peaks 504 may become very uncomfortable for the amputee.

In contrast, FIG. 6 illustrates the damped oscillations 602 of the stimulus produced by the electronic circuit 402 of the apparatus 102 (FIG. 1). The smooth, attenuating pulses, one of which is indicated by reference number 604, resemble the curved waveform produced by the sound waves from a ringing bell. This results in stimuli which are more comfortable to the amputee than the sharp peaks 504 of the conventional waveform 502. Although the maximum magnitudes of the oscillations in FIG. 6 are all substantially equal, it should be understood that such magnitudes vary according to the pressure applied to the sensors 120 and 122.

In operation, the front contact 128 corresponds to the front pressure sensor 120 and the back contact 130 corresponds to the back pressure sensor 122. When sufficient pressure is applied as the external operation to the back sensor 122 near the heel 114 of the foot 106, the amputee feels a stimulus from the back contact 130 at the rear of the residual limb. Similarly, when sufficient pressure is applied as the external operation to the front sensor 120 at the ball of the foot, the amputee feels a stimulus from the front contact 128 at the front of the residual limb. As the amputee walks on the lower limb prosthesis 104, the alternating rear and front stimuli on the residual limb result in a sense of feel corresponding to that experienced in a normal limb at the heel and toe strike of the human foot during the gait cycle.

Returning briefly to FIG. 1, it will be appreciated that the electrical wiring 124 of the apparatus positioned in the ankle portion 108 and the foot portion 106 are subject to considerable mechanical stress from standing, walking, and running. Accordingly, the wiring 124 attached to the pressure sensors 120 and 122 should be able to withstand the rigors of physical pressure and repeated bending.

In some cases, the wiring 124 between the electronics unit 126 and the pressure sensors 120 and 122 can be divided into an upper portion 138 and a lower portion 140 connected by a conductive connector 142, such as epoxy adhesive, solder, a weld, or other connector. Any suitable conductor may be used for the upper portion 138 and the lower portion 140 of the wiring 124.

The ends of the wires are attached to the terminals of the pressure sensors 120 and 122 and to the conductor 138 by a suitable conductive epoxy adhesive, solder, a weld, or other connector. Each such connection is insulated in a conventional manner.

The Embodiment of FIG. 7

An apparatus constructed in accordance with the present invention is not limited to use with prosthetic limbs, but may be employed with a natural but sensory impaired limb as well. A disease, such as diabetes, or a traumatic injury to a limb may cause impairment or dysfunction of the sensory perceptions normally present in a limb. The present invention restores a type of area specific stimulus to such sensory impaired limbs.

Turning to FIG. 7, for example, an apparatus 702 constructed for use with a natural lower limb 704 in accordance with the present invention is shown. A foot sensor unit 706 is provided to contact the sole 708 of the foot 710. A back sensor group, such as a back pressure sensor 712, is located in the sensor unit 706 toward the heel 714 of the foot 710. A front sensor group, such as a front pressure sensor 716, is positioned in the foot pad 706 proximate to the ball 718 of the foot 710. Each of the sensors 712 and 716 have a sensor characteristic that describes what electrical characteristic the sensor uses to sense the external operation thereon. The sensor characteristic can be, for example, inductance, resistance, impedance, or another characteristic.

Wires 720 are connected to the terminals of the pressure sensors 712 and 716 and extended upward to an electronics unit 722 to form channels. It should be appreciated that the electronics unit 722 includes a circuit similar to the lower limb electronic circuit 402 (FIG. 4) previously described.

With continued reference to FIG. 7, it should be understood that the electronic circuit 402 is connected to the pressure sensors 712 and 716 and a set of output elements, such as contacts 724, 726, 728 and 730, in a manner similar to that previously described. The electronics unit 722 containing the electronic circuit 402 is typically secured to the natural limb 704 with a strap 732 or other connectors.

The contacts 724, 726, 728 and 730 are similar to the contacts 128, 130, 132 and 134 of the apparatus 102 first embodiment (FIGS. 1–4). Like the contacts 128, 130, 132 and 134, the contacts 724, 726, 728 and 730 may be fashioned from electrode pads commonly placed on a patient for heart monitoring. Any suitable wiring 734 may be used to connect the electronic circuit 402 with the contacts 724, 726, 728, and 730 and to the sensors 712 and 716 to form the channels.

The contacts 724, 726, 728, and 730 are placed in contact with an area of the limb 704 which has sensory perception. The front contact 724, corresponding to the front pressure sensor 716, is positioned toward the front of the limb 704, and the back contact 726, associated with the back pressure sensor 712, is located toward the back of the limb 704.

The common contacts 728 and 730 are positioned one on either side of the limb 704. A contact strap 736, which may be any conventional elastic or adjustable strap, or another connector is provided to hold the contacts 724, 726, 728, and 730 in place against the limb 704.

The wiring 720 of the natural lower limb apparatus 702, like the wiring 124 of the lower limb prosthesis apparatus 102 of FIG. 1, is subject to considerable physical stress. To withstand the effects of excessive wear, in some cases the wiring 720 may be segmented into an upper portion 738 and a lower portion 740.

The upper portion 738 of the wiring 720 may be any suitable conductor connected to the electronic circuit 402 in a conventional manner. The lower portion 740 of the wiring 720 may be any suitable conductor and is extended upward to the ankle area 742 of the limb 704, where it is joined to the upper portion 738 of the wiring 720 by a connector 744, such as a conductive epoxy adhesive, solder, a weld, or another connector. A connector, such as conductive epoxy adhesive, solder, a weld, or another connector may be used to connect the ends of the lower portion 740 of the wiring 720 to the contacts of the pressure sensors 712 and 716.

In operation, the embodiment 702 functions similar to the embodiment 102 previously described (FIGS. 1–4). Stimuli which can be felt are produced by the contacts 724 and 726 in proportional response to pressure against the sensors 712 and 716. Accordingly, the apparatus 702 restores sense of feel for the sole 708 of the foot 710 which has impaired sensory perception.

The Embodiment of FIGS. 8–15

Referring now to FIG. 8, shown therein and designated by the reference numeral 802 is a third embodiment of an apparatus constructed in accordance with the present invention. In this embodiment, the apparatus 802 is for use with a lower limb prosthesis 804 which is worn on the residual limb (not shown) of an amputee. The apparatus 802 employs digital processing to provide sensory data to the amputee.

The lower limb prosthesis 804 has a foot portion 806, an ankle portion 808, and a socket portion 810. The socket portion 810 receives the residual limb of the amputee (not shown). The foot portion 806 includes a sole 812, a heel 814, a ball of the foot 816, and a toe 818.

A sensor unit 820 is attached to, or integrated in, the sole 812 of the foot portion 806. The sensor unit 820 senses an external operation thereon. For example, the sensor unit 820 can sense heat, cold, pressure, or another external operation. Preferably, the sensor unit 820 senses pressure. The sensor unit 820 is connected by wiring 822 to an electronics unit 824.

The electronics unit 824 comprises an electronic circuit with a processing and control center, yet to be described, contained within an enclosure. The electronics unit 824 is attached to, or integrated into, the lower limb prosthesis 804 where it is accessible for adjustment and repair.

Referring still to FIG. 8, the apparatus 802 includes output elements, such as four contacts 826, 828, 830, and 832, which are positioned in the socket portion 810 of the prosthesis 804. A front contact 826 is positioned so as to contact the front of the residual limb. A back contact 828 is positioned so as to contact the back of the residual limb. A first common contact 830 is positioned on the left of the residual limb, and a second common contact 832 is positioned on the right of the residual limb.

The left and right common contacts 830 and 832 are floating ground contacts, and the front and back contacts 826 and 828 are non-floating ground contacts. Therefore, a potential difference is created between the front contact 826 and the left common contact 830 or between the back contact 828 and the right common contact 832, respectively. A potential difference occurs when the electric charge at one point in the circuit is not the same as the electric charge at another point in the circuit. This potential difference allows the current to flow through the residual limb from the more positive contact to the more negative contact, thereby completing the circuit path.

The contacts 826, 828, 830, and 832 are connected by wiring to the electronics unit 824. A separate channel 834, 836, 838, and 840 connects each of the contacts 826, 828, 830, and 832, respectively, to the electronics unit 824. A portion of an electric circuit path is completed between the sensor unit 820 and the electronics unit 824 through the wiring 822. The circuit path is completed from the electronics unit 824 to the front contact 826 or the back contact 828 through the front channel 834 or the back channel 836, through the residual limb, to a common contact 830 or 832, and from the common contact 830 or 832 to the electronic unit 824 through the common channel 838 or 840.

FIG. 9 illustrates the processing method that occurs in the apparatus 802. With reference to FIG. 8 and FIG. 9, a power source 902 in the electronics unit 824 transmits an electrical input signal to the control and processing center 904. The electrical input signal has a current and a voltage, each with a magnitude, when the an electrical circuit is closed. When an external operation, such as pressure, is applied to one or more groups of sensors 906 in the sensor unit 820, the sensors input a sensory input in a sensory input signal that is processed by the control and processing center 904.

Each of the sensory output signals have a stimulus with a stimulus magnitude. The stimulus can be the current, voltage, or frequency. The stimulus is the component of the sensory output signal that is varied to provide the sensations to the user of the prosthetic device. Generally, the current is the stimulus so that the magnitude of the current is being increased or decreased.

The control and processing center 904 processes the sensory input signals and applies the processed sensory input signals to the electrical input signal to control the output of the electrical input signal. The sensory output signals are transmitted from the control and processing center 904 on separate channels to one or more contacts 908.

In the preferred apparatus, the control and processing center 904 has a processor 910 and an isolator 912. The isolator 912 receives the electrical input signal from the power source 902. The processor 910 receives the data from the sensory input signals and processes the data to determine the characteristics of each control signal. The control signals are sent to the isolator 912 where they are applied to the electrical input signal to create the sensory output signals.

The control signals are used by the isolator 912 to control the output of the electrical input signal in the same manner as the water system analogized to above. Thus, the magnitude of the stimulus of the sensory output signals is controlled by the control signals. Therefore, when a current is sent to the contacts 908 as the stimulus in the sensory output signals, the magnitude of the current can be set and varied for each sensory output signal.

Because the data in the sensory input signals is first processed and then used to control the output of the electrical input signal, a different sensory output signal can be transmitted on a different designated channel to a designated contact. Thus, for example, the front contact 826 can receive a pulsating current as the stimulus in a sensory output signal over the front channel 834, and the back contact 130 can receive a different pulsating current as the stimulus in a sensory output signal over the back channel 836.

Preferably, the proportion of the collective magnitude of the stimuli in each of the sensory output signals is proportional to the external operation at the respective groups of sensors. Thus, if seventy percent of the external operation is sensed by a front group of sensors, seventy percent of the stimuli is transmitted to the front contact.

Moreover, the collective magnitude intensity is divided with respect to an absolute reference. Thus, the collective magnitude of the current is allocated at one-hundred percent of the total magnitude from the zero output level. Other systems use a floating reference that jumps to the one-hundred percent level when force is applied, but then stabilize to zero when the pressure no longer increases, even though force is still applied. Then, when the force is released, the floating reference jumps to a negative one-hundred percent magnitude and then stabilizes to zero. Thus, the absolute reference used by the current system provides a higher comfort level.

In some cases, it is desirable to control the frequency rate of the sensory output signals as well as the current magnitude. In such a case, the frequency of the electrical input signal is controlled or modified at the power source 902 before the electrical input signal is transmitted to the isolator 912. This is accomplished by the processor 910 and a frequency controller 1002. The processor 910 transmits a control signal to the frequency controller 1002 designating a modified frequency. The frequency controller 1002 then modifies the frequency response of the electronics circuit at the power source 902. This allows the frequency controller 1002 to modify the frequency of the electrical input signal.

FIG. 11 illustrates the sensor unit 820 of the present invention. The sensor unit 820 can be integrated into the prosthesis 804 (see FIG. 8) or used as a pad on the sole 812 of the prosthesis 804. In either case, the sensor unit 820 can incorporate a series of slots 1102 to provide the sensor unit with flexibility.

Preferably, the sensors 906 are grouped into a front group and a back group. The front of the sensor unit 820 has a front group comprising four sensors: a front right sensor 1104, a front middle right sensor 1106, a front middle left sensor 1108, and a front left sensor 1110. Similarly, the back of the sensor unit 820 has a back group comprising four sensors: a back right sensor 1112, a back middle right sensor 1114, a back middle left sensor 1116, and a back left sensor 1118. Each of the sensors 1104, 1106, 1108, 1110, 1112, 1114, 1116, and 1118 have a sensor characteristic that describes what electrical characteristic the sensors use to sense the external operation thereon. The sensor characteristic can be, for example, inductance, resistance, impedance, capacitance, or another characteristic. Each of the sensors 1104, 1106, 1108, 1110, 1112, 1114, 1116, and 1118 are connected to a sensor controller 1120 by a trace 1122 or a wire.

A trace 1122 is an electrically conductive line that connects two or more points. Generally, traces are found on a circuit boards of various types. However, in this instance, the trace and the sensors 1104, 1106, 1108, 1110, 1112, 1114, 1116, and 1118 are inlaid in a flexible material, such as a flexible plastic.

Current flows from the sensor controller 1120, through the trace 1122, and to a respective one of the sensors. A common return 1124 completes the circuit path by returning the current pulses to the sensor controller 1120 as the sensory inputs in the sensory input signals. The sensor controller 1120 communicates the sensory input signals to the control and processing center 904 (FIG. 9).

Referring now to FIG. 11 and FIG. 12, the sensor unit 820 has three layers. The first layer 1202 contains the sensors 906 and the traces 1122. (For simplicity, when the sensors 1104, 1106, 1108, 1110, 1112, 1114, 1116, and 1118 are referred to as a group, the reference numeral 906 will be used to refer to all the sensors.) The second layer 1204 comprises an insulating layer. The third layer 1206 is a conducting layer.

The sensors 906 in the first layer 1202 are inductance-based pressure sensors. Preferably, each of the sensors 906 is an inductor coil pressure sensor. The inductor coil pressure sensor alleviates difficulties that may be present in other types of pressure sensors. The inductor coil sensor is rugged. Although the structure of the sensors 906 resists creasing, if the sensor becomes compressed, bent, or creased, the reaction of the pressure sensor does not vary as in other types of sensors; the inductance does not change. Other types of sensors that become bent or creased introduce error into the measurement of the pressure. Thus, the inductance coil pressure sensor provides more reliable measurements and increased durability when subjecting to creasing forces and repeated stress.

The second layer 1204 insulates the first layer 1202 from the third layer 1206, thereby providing a buffer between them. As the pressure on the sensor unit 820 is increased, the second layer 1204 compresses. As the second layer 1204 compresses, the coils of the first layer 1202 get closer to the conducting third layer 1206, thereby changing the inductance for the sensor.

The second layer 1204 comprises a foam rubber layer that has a low compression value and good resilience. A cellular urethane having a durometer ("shore A" scale) in the range of approximately ten to thirty is appropriate. One cellular urethane product that is suitable for use with the present invention is the PORON® brand cellular urethane which has a durometer of 15 and which is made by Rogers Corporation in Rogers, Conn. Equivalents also may be used.

The third layer 1206 comprises a metallic foil. Aluminum foil is preferred. The third layer 1206 completes the inductance coil pressure sensor by acting analogous to the "sore" of an inductor. The third layer completes the circuit by conducting the inductance response from the inductance coils in the first layer 1202 to the sensor controller 1120 via the common return 1124.

Turning to FIG. 13, the components of the sensor controller 1120 are shown. The sensor controller 1120 contains an oscillator 1302 and a multiplexer 1304.

The oscillator 1302 is connected to the common return 1124 from the sensors 906 (see FIG. 11), to the control and processing center 904, and to the multiplexer 1304. The oscillator 1302 receives an electrical power signal from the power source (not shown) and oscillates it. The oscillating electrical power signal is transmitted through the multiplexer 1304 to one of the sensors 906. The oscillator returns the sensory input signals to the control and processing center 904.

The multiplexer 1304 is connected to the sensors 906, to the control and processing center 904, and to the oscillator 1302. The multiplexer 1304 receives a processor control signal from the control and processing center 904 designating one of the sensors to receive the electrical power signal. Based upon the processor control signal, the multiplexer 1304 routes the oscillating electrical power signal from the oscillator 1302 to the designated one of the sensors 906.

Referring to FIG. 14, the elements of the electronics unit 824 are illustrated. The electronics unit 824 has a power source 902 and a control and processing center 904. The power source 902 provides electrical power to the other components of the electronics unit 824 and to the sensor unit 820 (FIG. 8). The control and processing center 904 communicates with the sensor controller 1120 and with the contacts 908.

The control and processing center 904 receives the sensory input signals from the sensor controller 1120 and processes the data in the sensory input signals with the electrical input signal from the power source 902 to create the sensory output signals that are transmitted to the contacts 908. Several components complete the processing in the control and processing center 904. The components of the control and processing center 904 include a process converter 1404, a frequency counter 1406, and an options controller 1408. The process converter 1404, which processes the sensory input signals to create a plurality of control signals that are transmitted to the isolator 912, comprises the processor 910 and a signal converter 1410.

The frequency counter 1406 receives the sensory input signals from the sensor controller 1120 within a time window. The time window is regulated by the processor 910. The processor 910 allows the frequency counter 1406 to receive the sensory input signals within the time window and then disables the frequency counter 1406 until another measurement is to be taken. Preferably, the time window is one milli-second.

The frequency counter 1406 receives the sensory output signals as a series of pulses. Thus, the frequency counter 1406 collects and measures the number of pulses that are received within the time window. The data from the sensory input signals is transferred as a series of binary numbers to the processor 910 in the process converter 1404.

In one version of the present invention, the frequency counter 1406 is comprised of a twelve bit binary counter and a shift register. The twelve bit counter reads the pulse values of the sensory input signals from the sensor controller 1120. The twelve bit counter transmits the pulse values as binary numbers to the shift register in a parallel communication link. The shift register acts as a temporary storage medium. After a period of delay, the shift register sends the pulse values serially to the processor 910 of the process converter 1404.

The options controller 1408 allows a user to set control options for the electronics unit 824. For example, a user can set the minimum and the maximum magnitudes of current which will be transmitted from the isolator 912 to the contacts 908 as the stimulus in the sensory output signals. Also, the user can set the electronics unit 824 to send sensory output signals to the contacts 908 only after pressure on the sensors 906 has exceeded a pressure threshold or after the time of which pressure has been exerted on the sensors 906 has exceeded a time threshold.

The process converter 1404 receives the sensory input signals from the frequency counter 1406 and processes the sensory input signals to create a plurality of control signals that are transmitted to the isolator 912. The control signals control the output of the electrical input signal by setting and controlling the stimulus, including the stimulus magnitude, of the sensory output signals.

The processor 910 controls the sensing, processing, and stimulus output in the apparatus 802 (FIG. 8). The processor 910 has associated memory to store data and the programming. The processor 910 also processes the sensory input signals. The processor 910 selects a designated one of the sensors 906 from which to receive a sensory input signal having sensory input.

The processor 910 has a processing program which it uses to process the sensory input signals to create intermediate control signals. Intermediate control signals are transmitted to the converter 1410. Because the preferred system has four separate channels leading to four contacts 908, the processor 910 creates four intermediate control signals, each designated to control the sensory output signal to one of the contacts.

The converter 1410 receives the intermediate control signals from the processor 910 and translates the intermediate control signals into control signals that can be received and processed by the isolator 912. The converter 1410 transmits the control signals to the isolator 912.

Preferably, the converter 1410 is a digital potentiometer. The intermediate control signals cause the converter 1410 to output a value to the isolator 912, which when used by the isolator 912, represents a resistance value for each control signal. The converter 1410 converts the intermediate control signals to control signals and transmits the four control signals to the isolator 912.

The isolator 912 isolates the electronic components in the electronics unit 814 from the high voltage of the power source 902. This helps prevent the high voltage from damaging components such as the converter 1410 and the processor 910.

The isolator 912 receives the electrical input signal from the power source 902 and the control signals from the converter 1410 in the process controller 1404. The isolator 912 uses the control signals to control the output of the electrical input signal. The isolator 912 applies the control signals to the electrical input signal to create the sensory output signals. The isolator 912 sends the sensory output signals to the contacts 908 through the channels. Each sensory output signal is designated for a designated contact.

In the preferred system, the isolator 912 is an opto-isolator (OI) chip with four OIs, one designated for each of the contacts 908. An OI has a light emitting diode component (LED) and a resistive photo-cell component (RPC) which is generally a cadmium sulfide (CDS) RPC. The LED and the RPC are paired together so that the LED is the input of the OI, and the RPC is the output of the OI.

The LED of the OI receives the control signal from the converter 1410. The control signal has a voltage level that causes the LED to emit light having an intensity level. A higher voltage level in the control signal causes the LED to emit a greater intensity light.

The RPC portion of each isolator 912 receives the electrical input signal. The RPC portion of the isolator 912 also receives the light from its corresponding LED. The RPC converts the light into a resistance value. The resistance value corresponds to the intensity of the light emitted from the LED. Therefore, a greater intensity light from the LED corresponds to a higher resistance value in the RPC.

The resistance value is applied to the electrical input signal in the RPC. Since each RPC receives the same amount of voltage because each receives the electrical input signal, the resistance value in the RPC controls the level of current sent to each contact as the stimulus in the sensory output signal. The output from each RPC is the sensory output signal that is sent to each respective contact.

It will be appreciated that any suitable isolator may be used. For example, an LED and an NPN transistor pair may be substituted for each LED-RPC pair. This is an example of an analog-switch semiconductor substitution solution.

The power source 902 comprises a battery 1412 and a transformer 1414, yet to be described. The battery 1412 powers the frequency counter 1406, the processor 910, and the transformer 1414 with an electrical power signal. In addition, the battery 1412 sends the electrical power signal to the sensor controller 1120. The electrical power signal has a voltage with a magnitude. The electrical power signal is transferred by the sensor controller 1120 to the sensors 906.

The transformer 1414 receives the power from the battery 1412. The transformer 1414 oscillates the electrical power signal. The transformer 1414 also transforms the voltage to a high voltage level which is preferably between approximately 100 volts and 150 volts, although a different range may be used. The transformer 1414 outputs the oscillating-transformed electrical power signal as an electrical input signal to the isolator 912.

The frequency of the electrical input signal can be modified. This can be accomplished by transmitting a frequency control signal from the process converter 1404 to the transformer 1414.

The processor 910 in the process converter 1404 can be configured to modify the frequency of the electrical input signal. The processor 910 transmits a fifth intermediate control signal to the converter 1410. The converter 1410 converts the intermediate control signal into a resistance value which is applied as an input to the transformer 1414. Because the transformer 1414 has resistance and capacitance, and because the frequency of the electrical output signal is governed by the relationship that the frequency is equal to one divided by the quantity of the resistance multiplied by the capacitance of the transformer 1414 [$f=1/RC$], a change in the resistance in the transformer circuit causes a change in the frequency of the electrical input signal which is output from the transformer 1414.

In addition, the processor 910 can be configured to turn the transformer 1414 on and off When the sensors 906 are not transmitting sensory input signals, the processor 910 turns the transformer off. This allows the battery 1412 to conserve energy. When the sensors 906 are transmitting sensory input signals, the processor 910 turns the transformer 1414 on, and the transformer then transmits the electrical input signal to the isolator 912.

FIG. 15 illustrates the components of the transformer 1414 in operation with the processor 910, the isolator 912, and the contacts 826, 828, 830, 832. The transformer 1414 comprises a 47 µf capacitor 1502 connected to the battery. A 120Ω resistor 1504 is connected to a node with the capacitor 1502. The other side of the resistor 1504 is connected to a one KΩ resistor 1506 which is connected at a node to both a 3.9 KΩ resistor 1508 and the gate of a transistor 1510. The cathode of the transistor 1510 at the node between the capacitor 1502 and the 120Ω resistor 1504. The anode of the transistor 1520 goes to the input of a transformer chip 1512. The transformer chip 1512 has a 1:30 winding ratio of input to output. One transformer chip 1512 output is attached to the node between the battery 1412 and the capacitor 1502.

The front contact 826 and the back contact 828 are connected through the OIs 1516 and 1518, respectively, of the isolator 912 to the node between the 120Ω resistor 1504 and the 1 KΩ resistor. Likewise, the common contacts 830 and 832 are connected through the OIs 1520 and 1522, respectively, of the isolator 912 to the transformer chip 1512. The OIs 1516, 1518, 1520, and 1522 are illustrated as a variable resistor symbol with a "DP" under the symbol to represent the digital processing in the processor 910, the transfer of the intermediate control signals to the converter 1410, and the output of the control signals from the digital potentiometers in the converter 1410 to the isolator 912. (See FIG. 14.) Each contact 826, 828, 830, 832 is connected to a respective OI through a separate channel 1524, 1526, 1528, and 1530, respectively.

FIG. 14 illustrates the components used in conjunction with the processor 910 to turn the transformer 1414 on and off. The transformer 1414 only operates when a sufficient power signal, having sufficient voltage, is transmitted from the processor 910. The diode 1514 prevents voltage flow from the transformer 1414 to the processor 910, but allows current to flow from the processor to the transformer.

If the processor 910 configures the transformer 1414 to be off, the processor does not allow power to be transferred to the gate of the transistor 1510. When the processor 910 determines that the transformer 1414 is to be on, the processor transfers power to the gate of the transistor 1510. When the voltage at the gate of the transistor 1510 is slightly higher than the voltage at the cathode, voltage is pulled through the anode so that the transformer chip 1512 is energized. The transformer chip 1512 transforms the voltage to a high voltage, the output being thirty times greater than the input. The high voltage exits the transformer chip 1512 and passes through the resistor-capacitor (RC) network of the circuit so that the electrical input signal oscillates at a frequency dictated by the RC circuit.

The oscillating high voltage signal is output as the electrical input signal to each OI 1516, 1518, 1520, and 1522 in the isolator 912. The control signals are applied at the OIs 1516, 1518, 1520, and 1522, and the result is transmitted to the respective contacts 826, 828, 830, 832 through respective channels 1524, 1526, 1528, and 1530 as the sensory output signals. Thus, it can be appreciated that the control signals are applied to the electrical input signal in the respective OIs 1516, 1518, 1520, and 1522 of the isolator 912 to create the sensory output signals which are then transmitted to the respective contacts 826, 828, 830, and 832.

With reference now to FIGS. 11–15 the operation of the apparatus 802 (FIG. 8) is described. While the apparatus 802 is operational, the battery 1412 powers the oscillator 1302 in the sensor controller 1120 with the electrical power signal. The oscillator 1302 has an associated capacitor which fires, causing the electrical power signal to have an oscillating square wave frequency response. Because the output of the oscillator 1302 is one of the inputs of the multiplexer 1304, the multiplexer can always transmit the oscillating power signal to the sensors 1104, 1106, 1108, 1110, 1112, 1114, 1116, or 1118 (collectively, the sensors 906).

At the outset, the processor 910 determines which of the sensors 906 should be polled. That is, the processor 910 determines from which of the sensors 906 the processor will obtain a pressure measurement. Generally, the processor 910 polls all of the sensors 906 sequentially starting with the upper right sensor 1104.

The processor 910 transmits a processor control signal to the multiplexer 1304 designating which of the sensors 906 is to be polled. In response to the processor control signal, the multiplexer 1304 transmits the oscillating electrical power signal to the designated one of the sensors 906 through the required trace 1122.

When the designated sensor 906 is polled, the electronics unit 824 of the apparatus 802 measures the frequency response of the system. The frequency response is the number of pulses triggered within a given window of time. The inductance changes as the coil layer 1202 gets closer to the foil layer 1206 of the sensor unit 820. Therefore, the frequency changes as the inductance in the inductance-based pressure sensor changes. The frequency change is the change of the neper frequency which is equal to the resistance divided by the quantity of two multiplied by the inductance [$\alpha=R/2L$], wherein the resonant frequency is equal to one over the square root of the quantity of the inductance multiplied by the capacitance [$\omega_0=1/\sqrt{LC}$].

The frequency pulses are returned as sensory input data in a sensory input signal through the foil layer 1206, to the common return 1124, and to the oscillator 1302. The oscillator 1302 transmits the sensory input signal to the frequency counter 1406 in the control and processing center 904.

The frequency counter 1406 receives the pulses of the sensory input signal within the time window allocated by the processor 910. One milli-second after the processor 910 enables the frequency counter 1406, the processor disables the frequency counter so that no more pulses are counted. The frequency counter 1406 transfers the sensory input signal's pulse data to the processor 910 as a series of binary numbers.

The processor 910 completes the sensor polling procedure for all of the sensors 906 in a like manner. The processor 910 then processes all of the sensory input signals. In the preferred method, the processor 910 adds all of the sensory input signals from the front sensors 906 to get a single front sensor magnitude. The processor 910 completes the same process for the back sensors, for the four sensors on the right half of the sensor unit 820, and for the sensors on the left half of the sensor unit. This results in a single front sensor magnitude, a single back sensor magnitude, a single right sensor magnitude, and a single left sensor magnitude. The processor 910 uses these sensor magnitudes to determine what type of stimulus, including the stimulus magnitude, is to be sent to each of the contacts 908 in the sensory output signals.

The processor 910 next transmits four intermediate control signals to the converter 1410. Each intermediate control signal is designated to control a designated sensory output signal to a designated contact 826, 828, 830, or 832. At the same time, the processor 910 enables the transformer 1414. In addition, if the processor 910 has been configured to control the frequency of the electrical input signal, the processor will send a separate frequency control signal to the converter 1410.

It shall be recalled that the converter 1410 is a series of digital potentiometers. Essentially, the converter 1410 is a digital-to-analog converter. The converter 1410 is wired to transmit four separate control signals to four OIs 1516, 1518, 1520, and 1522 in the isolator 912. After the converter 1410 receives the intermediate control signals, it converts each intermediate control signal to a control signal having a designated voltage magnitude and transmits the control signals to the isolator 912.

In addition, if the frequency control signal was sent to the converter 1410, the converter will "output" a resistance level to the transformer 1414. Since a fifth digital potentiometer output is wired to the transformer 1414, merely placing the resistance value in the circuit causes the frequency change. The level of the resistance is controlled by the frequency control signal originated by the processor 910.

The isolator 912 receives both the electrical input signal from the transformer 1414 and the control signals from the converter 1404. The isolator 912, using the OI LED-RPC pairs, converts each voltage magnitude from each control signal into a resistance value. Each resistance value is individually applied to the electrical input signal (as illustrated in FIG. 15) to create each sensory output signal.

Each sensory output signal is transmitted over its designated channel 1524, 1526, 1528, or 1530 to its designated contact 826, 828, 830, or 832. Each sensory output signal has a stimulus having a selected current magnitude and a selected frequency individually created for each individual contact 826, 828, 830, or 832.

Because some of the contacts 830 and 832 are floating grounds, a potential difference is created between the contacts 826, 828, 830, and 832. This allows the current from the sensory output signals to flow from the front or back contact 826 or 828, through the limb, and to a common contact 830 or 832 to be returned to the isolator 912, thereby completing the circuit path.

It will be appreciated that the apparatus 802 can be configured to provide different types of sensory output signals for different events. For example, the processor 910 can be configured to only initiate stimulus to the contacts when the pressure on the front sensors is not in equilibrium with the pressure on the back sensors. Alternately, the processor 910 can be configured to initiate stimulus to the contacts when the pressure on the sensors exceeds a pressure threshold. Another option is to initiate stimulus to the contacts when a pressure threshold is exceeded for more than a certain amount of time defined by a window of time of a time threshold.

The Embodiment of FIG. 16

A digital processing apparatus constructed in accordance with the present invention is not limited to use with prosthetic limbs, but may be employed with a natural but sensory impaired limb as well. The present invention restores sensation to sensory impaired limbs.

Turning to FIG. 16, for example, an apparatus 1602 constructed in accordance with a fourth embodiment of the present invention is illustrated. The apparatus 1602 is for use with a natural lower limb 1604. The apparatus 1602 employs digital processing to provide sensory information to the prosthetic device user.

The natural limb 1604 has a foot 1606 and an ankle 1608. The foot 1606 has a sole 1610, a heel 1612, a ball of the foot 1614, and a toe 1616.

A sensor unit 1618 is placed under the sole 1610 of the foot 1606. The sensor unit 1618 senses an external operation thereon. For example, the sensor unit 1618 can sense heat, cold, pressure, or another external operation. Preferably, the sensor unit 1618 senses pressure. The sensor unit 1618 is connected by wiring 1620 to an electronics unit 1622.

The electronics unit 1622 comprises an electronic circuit with a processing and control center, as described above, contained within an enclosure. The electronics unit 1622 is attached to the natural limb 1604 where it is accessible for adjustment and repair.

Referring still to FIG. 16, the apparatus 1602 includes four output elements, such as contacts 1624, 1626, 1628, and 1630, which are positioned on the natural limb 1604. A front contact 1624 is positioned so as to contact the front of the natural limb 1604. A back contact 1626 is positioned so as to contact the back of the natural limb 1604. A first common contact 1628 is positioned on the left of the limb 1604, and a second common contact 1630 is positioned on the right of the limb 1604.

The left and right common contacts 1628 and 1630 are floating ground contacts, and the front and back contacts 1624 and 1626 are non-floating ground contacts. A potential difference is created between the front contact 1624 and the left common contact 1628 or between the back contact 1626 and the right common contact 1630, respectively. A potential difference occurs when the electric charge at one point in the circuit is not the same as the electric charge at another point in the circuit. This potential difference allows the current to flow through the residual limb from the more positive contact to the more negative contact, thereby completing the circuit path.

The contacts 1624, 1626, 1628, and 1630 are connected by wiring to the electronics unit 1622. A separate channel 1632, 1634, 1636, and 1638 connects each of the contacts 1624, 1626, 1628, and 1630, respectively, to the electronics unit 1622. A portion of an electric circuit path is completed between the sensor unit 1618 and the electronics unit 1622 through the wiring 1620. In addition, part of the circuit path is completed from the electronics unit 1622 to the front contact 1624 or back contact 1626 through the front channel 1632 or the back channel 1634, through the residual limb, to a common contact 1628 or 1630, and from the common contact 1628 or 1630 to the electronic unit 1622 through the common channel 1636 or 1638.

The Embodiment of FIGS. 17–20

Referring now to FIGS. 17 and 18, an apparatus 1702 constructed in accordance with the present invention for an upper extremity prosthesis is illustrated. FIG. 17 shows a hand component 1704 of the upper extremity apparatus 1702, and FIG. 18 shows a socket component 1802 of the upper extremity apparatus 1702.

The hand component 1704 is connected to the socket component 1802 by means of a conventional "OTTO BOCK" bushing. One connector portion 1706 of the bushing is secured in the wrist area of the hand component 1704, and the other connector portion 1804 of the bushing is attached to the socket component 1802. The two portions 1706 and 1804 of the "OTTO BOCK" bushing connect together to secure the hand component 1704 to the socket component 1802. The bushing allows the hand 1704 to pivot while achieving electrical connections to operate the hand 1704.

As shown in FIG. 17, the hand component 1704 may have a shell 1708 which is covered by a glove 1710. The "OTTO BOCK" bushing connector 1706 is secured inside the shell 1708 and is electrically connected to the hand motor 1712 of a conventional gripping mechanism (not shown).

The hand component 1704 preferably has the normal five digits: a thumb 1714, an index finger 1716, a middle finger (not shown), a ring finger (not shown), and a little finger (not shown). The thumb 1714 and index finger 1716 may be adapted for primary movement and the other fingers may be generally designed to follow the movement of the index finger 1716.

The apparatus 1702 includes a sensor 1718 secured to the surface of the thumb 1714. The sensor 1718 may be resistance-based or inductance-based. Suitable resistance-based sensors include the DYNAFORCE pressure sensor and the FORCE SENSING RESISTOR™ previously described. A suitable inductance-based sensor is the inductance-based coil sensor of the present invention previously described. Pressure sensors may be located at other areas of the prosthetic hand. Pressure sensors may be placed in one or more of the fingers of the prosthetic hand, for example, to provide a wider surface area of perception for the amputee.

The pressure sensor 1718 preferably is attached to a flattened portion of the shell 1708 with an epoxy adhesive. The flattened area around the sensor 1718 is built up with epoxy to achieve the proper shape for a thumb 1714. If the sensor 1718 is resistance-based, it should not be bent or physically stressed in its installation or it may falsely indicate that an object is being grasped by the hand 1704.

A pair of wires 1720 and 1722 are attached to the electrical contacts of the sensor 1718. The wires 1720 and 1722 can be any conventional wiring.

A connector 1724, such as adhesive tape, connects the wires 1720 and 1722 to the thumb 1714 near the sensor 1718 to prevent physical stress on the connection between the wires 1720 and 1722 and the sensor 1718 when the hand 1704 is opened and closed. The wires 1720 and 1722 extend along the thumb 1714, between the index finger 1716 and middle finger, and back to the wrist area of the hand 1704 near the "OTTO BOCK" bushing connector 1706. Slack is provided in the wires 1720 and 1722 to accommodate the movement of the hand 1704.

The wires 1720 and 1722 extend through an incision (not shown) in the hand shell 1708 and connect to the metallic conductors (not shown) of the "OTTO BOCK" bushing connector 1706. Conductive epoxy or another suitable connector is used to join the wires 1720 and 1722 to the sensor 1718 terminals and to the "OTTO BOCK" bushing terminals. The connections are insulated to prevent a short circuit.

As illustrated by FIG. 18, the socket component 1802 of the upper extremity apparatus 1702 is adapted to receive the residual limb 1806. The apparatus 1702 provides physical sensations to the surface of the residual limb 1806 by means of a battery-powered, vibrating motor 1808 positioned so as to communicate vibrations to the limb when the limb is received in the socket component 1802.

The vibrating motor 1808 is operated by an electronics unit 1810 supported inside the socket component 1802 and connected to the "OTTO BOCK" bushing terminals. The connections are insulated to prevent a short circuit.

The electronics unit 1810 and the vibrating motor 1808 are powered by a circuit battery 1812. To eliminate the need for frequent battery replacement, the preferred circuit battery 1812 is a rechargeable Nicad 3-volt d.c. battery. The circuit battery 1812 is trickle charged by a myo-electric battery 1814, such as a standard 6-volt or 9-volt d.c. battery, and which is also supported inside the socket component 1802 and connected to the electronics unit 1810. The myo-electric battery 1814 also is electrically connected through the "OTTO BOCK" bushing 1706 and 1804 to power the hand motor 1712 which operates the gripping mechanism in the hand component 1704.

The vibrating motor 1808 preferably is the type used in pager devices to signal the wearer by vibration rather than audible sound to respond to a page. The number 208004 vibrating motor available from NEC America (Dallas, Tex.) is a suitable vibrating motor 1808 for use with the upper extremity apparatus 1702. Such a vibrating motor 1808 is about one inch in length and has a diameter slightly larger than a pencil.

Attention now is directed to FIG. 19 for a description of the electronic circuit 1902 contained within the electronics unit 1810 (FIG. 18). The electronic circuit acts as an analog control and processing center. As indicated by broken lines, the upper extremity electronic circuit 1902 generally includes a trigger circuit 1904, a delay circuit 1906, a switch 1908, a vibrating motor control circuit 1910 and a trickle charging circuit 1912.

The trigger circuit 1904 is piggybacked into the hand motor 1712 between the hand motor and the bi-directional motor control 1914 to detect muscle activity in the residual limb which is sensed by the sensors (not shown) of the bidirectional motor control. The trigger circuit 1904 is also connected to the delay circuit 1906 to provide an output to the delay circuit 1906 in response to muscle activity in the residual limb. The trigger circuit 1904 preferably is adjusted to respond to a level of muscle activity which is insufficient to cause movement of the hand 1704 (not shown in FIG. 19). The trigger circuit 1904 includes a pair of 1N914 diodes 1916 and 1918 and resistors 1920 and 1922.

The trigger circuit 1904 connects to the input of the delay circuit 1906, which is the first of two SK9442 (A14) transistors 1924 and 1926 connected as a Darlington pair. In other words, the output of the first A14 transistor 1924 is the input to the second A14 transistor 1926.

The delay circuit 1906 also includes a 47 µf capacitor 1928, a resistor 1930, and a 1 MΩ potentiometer 1932. The potentiometer 1932 provides the capability to adjust the length of the "delay time," which is defined and described later herein.

The output of the delay circuit is connected to the switch 1908, which operates to turn the vibrating motor control circuit 1910 on and off. The switch 1908 is a 5-volt d.c. single-pole single-throw electromechanical relay. A suitable device for the switch 1908 is the 275-240/Micromini 5VDC SPDT switch manufactured by Archer for Tandy Corporation's Radio Shack stores. The switch 1908 closes when it receives a signal from the delay circuit 1906, thereby energizing the vibrating motor control circuit 1910. The switch 1908 opens when it receives no signal from the delay circuit 1906, thereby de-energizing the vibrating motor control circuit 1910.

With continued reference to FIG. 19, the vibrating motor control circuit 1910 includes a 2N3906 transistor 1934, a 2N3904 transistor 1936, a 100 KΩ potentiometer 1938, a resistor 1940, and a capacitor 1942. The sensor 1718 is connected in series with the output of the 2N3906 transistor 1934 and the potentiometer 1938. The potentiometer 1938 is included to allow the amputee to adjust the magnitude of the stimuli produced. The potentiometer 1938 is a standard variable resistor in the range of 100 KΩ to 150 KΩ, depending upon the desired range of magnitude.

As mentioned previously, the electronic circuit 1902 receives power from the circuit battery 1812, which is trickle charged by the myo-electric battery 1814. The trickle charging circuit 1912 includes a resistor 1944 and a 1N914 diode 1946. The switch 1908 is connected to the circuit battery 1812 and the trickle-charging circuit 1912 in order to close and energize the vibrating motor control circuit 1910.

Returning to FIGS. 17 and 18, in operation the apparatus 1702 generally produces stimuli felt by the amputee when the hand 1704 is in motion or muscle activity is present in the residual limb 1804 and for a preset "delay time" after the muscle activity ceases. As long as muscle activity is present in the residual limb 1804, the trigger circuit 1904 is constantly resetting the delay cycle. Accordingly, while there is muscle activity, the delay time never expires and the apparatus 1702 remains energized or "on."

Once muscle activity in the residual limb 1804 ceases, the trigger circuit 1904 stops resetting the delay cycle. If there is no muscle activity for the length of the delay time, the delay circuit 1906 provides an "off" signal to the switch 1908 to open and de-energize the vibrating motor control circuit 1910.

In operating to de-energize the vibrating motor control circuit 1910, the delay circuit 1906 not only conserves circuit battery 1812 power but also enhances the comfort level of the amputee. If the amputee is grasping an object, such as a pencil or pen, for an extended period of time, the constant sensation of the vibrating motor 1808 may become annoying to the amputee. The amputee is aware that the object is in the grasp of the prosthetic hand and a constant reminder from the vibrating motor 1808 is unnecessary and uncomfortable. The delay circuit 1906 cuts off the vibrating motor 1808 at the end of the delay time to stop these unneeded sensations. It should be appreciated, however, that any new movement of the hand triggers another delay cycle and another period of stimuli. The 1 MΩ potentiometer 1932 provided in the delay circuit 1906 allows the amputee to adjust the duration of the delay time.

Now it will be appreciated that the delay feature may be implemented in the lower limb assembly, as previously described. Moreover, the damping circuit and the collective magnitude dividing circuit feature of the electronic circuit 402 of FIG. 4 may be implemented in the upper extremity apparatus and may be advantageous where pressure sensors are installed in more than one digit of the hand portion, such as the thumb and the index finger.

The vibrating motor 1808 is driven by the vibrating motor control circuit 1910 (FIG. 19) in direct proportion to the amount of pressure applied to the sensor 1718. As the pressure on the sensor 1718 is increased, the resistance of the sensor 1718 decreases, the current to the vibrating motor 1808 increases and the magnitude of the vibrations is augmented. Conversely, as pressure on the sensor 1718 is decreased, the strength of vibrations from the vibrating motor 1808 is reduced. When the combined resistance of the sensor 1718 and potentiometer 1938 is greater than approximately 1 MΩ, the vibrating motor control circuit 1910 is virtually an open circuit and the current is off.

When the combined resistance of the sensor 1718 and potentiometer 1938 (FIG. 19) is between 1 MΩ and 200 KΩ, the vibrating motor control circuit 1910 is on (assuming the switch 1908 is closed), but the intensity of the vibrations may not be perceptible to the amputee. At combined resistances below 200 KΩ for the potentiometer 1938 and the sensor 1718, the stimuli from the vibrating motor 1808 are generally felt by the amputee in direct proportion to the amount of pressure applied to the sensor 1718. Accordingly, the vibrating motor control circuit 1910 gives the amputee a sense of how tightly the prosthetic hand 1704 is gripping an object. The potentiometer 1938 allows the amputee to adjust the intensity of the vibrations to suit the personal comfort level of the amputee.

The vibrating motor 1808 may be a source of voltage spikes, current surges, or electrical noise which might interfere with the upper extremity electronic circuit 1902. The 10 μf capacitor 1942 is provided in the vibrating motor control circuit 1910 to isolate from the upper extremity electronic circuit 1902 any electrical spikes, surges, or noise produced by the vibrating motor 1808.

The single-pole single-throw electro-mechanical relay switch 1908 (FIG. 19) may produce an undesirable noise when opening and closing. In addition to silent operation, it is preferred that the switch be as lightweight and as small in size as possible.

Figure 20:
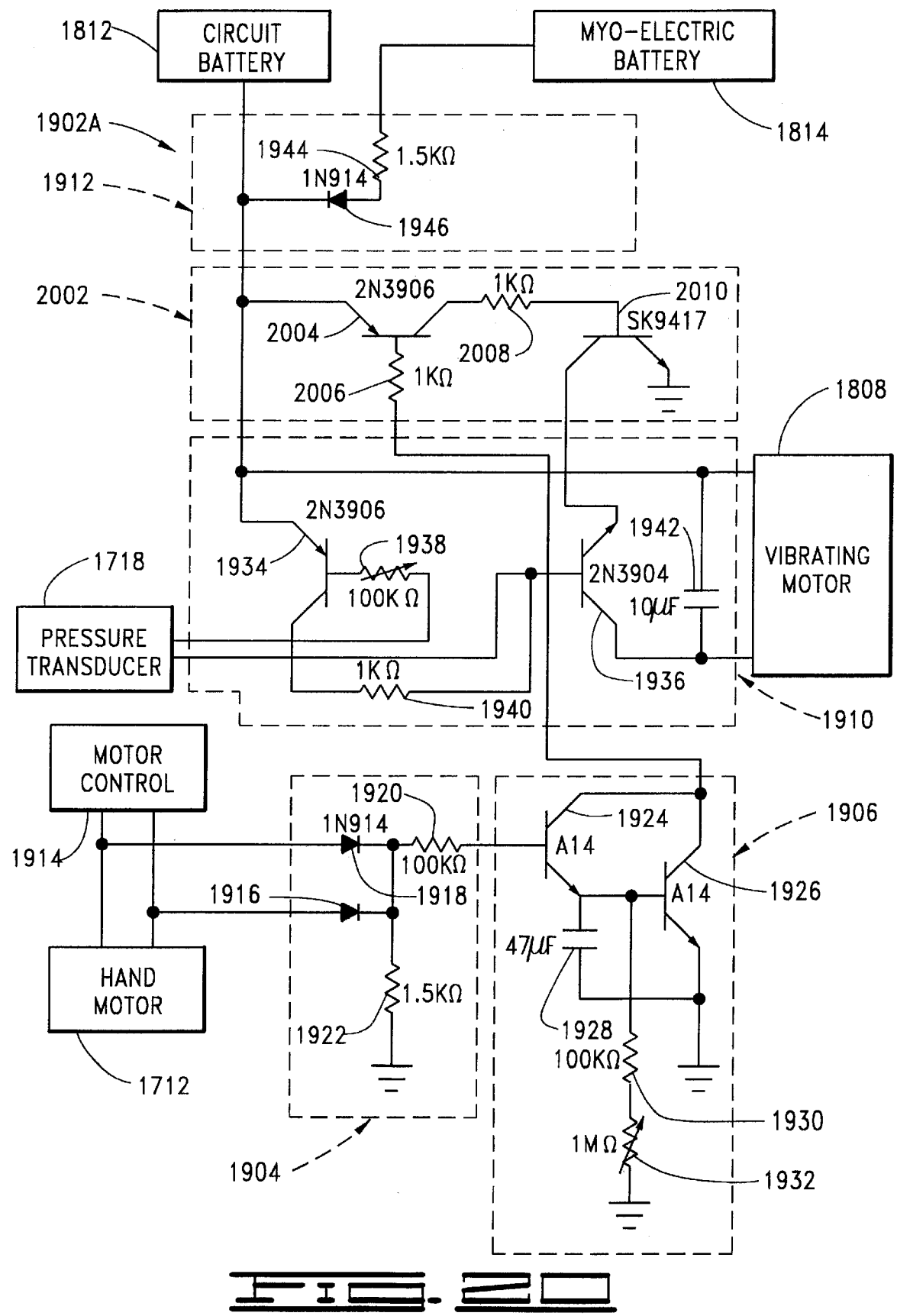
FIG. 20 is an electrical schematic of another preferred embodiment of the electronic circuit of the upper limb prostheses shown in FIGS. 17 and 18.

In order to provide a switch which is silent, light-weight and very compact, a transistorized switch may be substituted for the electro-mechanical switch 1908 in the upper extremity apparatus 1702. With reference to FIG. 20, an electronic circuit 1902A for the upper extremity apparatus 1702 utilizes a transistorized switch 2002 in place of the electro-mechanical switch 1908 of FIG. 19. With the exception of the switch 2002, the components of the circuit 1902A are the same as those of circuit 1902.

The switch 2002 includes a 2N3906 transistor 2004, two resistors 2006 and 2008, and an SK9417 transistor 2010. Because the emitter of the A14 transistor 1926 of the trigger circuit 1906 is grounded, a negative pulse is sent from the trigger circuit 1906 to trigger the switch 2002. A negative pulse from the trigger circuit 1906 causes the 2N3906 transistor 2004 to become conductive.

The 2N3906 transistor 2004 acts like an inverting buffer to the SK9417 transistor 2010. When the 2N3906 transistor 2004 receives a negative pulse from the trigger circuit 1906, it becomes "on" and provides a positive pulse to the SK9417 transistor 2010. The positive pulse causes the SK9417 transistor 2010 to saturate. This saturation of the SK9417 transistor 2010 makes the switch 2002 conductive between the circuit battery 1812 and the vibrating motor control circuit 1910 in a manner analogous to closing the electro-mechanical switch 1908 in the electronic circuit 1902A.

Changes may be made in the combinations, operations and arrangements of the various parts and elements described herein without departing from the spirit and scope of the invention as defined in the following claims.

What is claimed is:

1. A method for providing sensory perceptions in a sensor system of a prosthetic device, the method comprising:
    sensing an external operation magnitude from a plurality of sensor groups, each sensor group sensing a fraction of the external operation magnitude;
    generating a plurality of sensory inputs from the sensor groups in response to the external operation;

generating an electrical input signal with a magnitude;
controlling the electrical input signal with the plurality of sensory inputs to create a plurality of sensory output signals collectively having a stimulus with a collective stimulus magnitude corresponding to the electrical input signal magnitude, each sensory output signal having a fraction of the stimulus magnitude corresponding to the fraction of the external operation magnitude sensed by one of the sensor groups; and
transmitting each of the sensory output signals to a designated one of a plurality of contacts through a designated one of a plurality of channels;
wherein the plurality of contacts comprises a non-floating ground contact and a floating ground contact, and wherein the method further comprises creating a potential difference between the floating ground contact and the non-floating ground contact and creating a partial circuit path from the non-floating ground contact through a residual limb and then to the floating ground contact.

2. A method for providing sensory perceptions in a sensor system of a prosthetic device, the method comprising:
sensing an external operation magnitude from a plurality of sensor groups, each sensor group sensing a fraction of the external operation magnitude;
generating a plurality of sensory inputs from the sensor groups in response to the external operation, wherein the plurality of sensory inputs are in a plurality of sensory input signals;
generating an electrical input signal with a magnitude;
controlling the electrical input signal with the plurality of sensory inputs to create a plurality of sensory output signals collectively having a stimulus with a collective stimulus magnitude corresponding to the electrical input signal magnitude, each sensory output signal having a fraction of the stimulus magnitude corresponding to the fraction of the external operation magnitude sensed by one of the sensor groups; and
transmitting each of the sensory output signals to a designated one of each of a plurality of contacts through a designated one of a plurality of channels;
wherein controlling the output comprises:
processing the sensory input signals to create a plurality of control signals; and
controlling the electrical input signal with the control signals by applying the control signals to the electrical input signal to create the plurality of sensory output signals;
wherein the controlling the output step comprises digitally processing the electrical input signal with the plurality of sensory input signals;
wherein processing the sensory input signals comprises:
counting frequency pulse data in the sensory input signals within a discrete time frame; and
processing the frequency pulse data to determine the fraction of the stimulus magnitude to be generated in each of the sensory output signals.

3. A method for providing sensory perceptions in a sensor system of a prosthetic device, the method comprising:
sensing an external operation magnitude from a plurality of sensor groups, each sensor group sensing a fraction of the external operation magnitude;
generating a plurality of sensory inputs from the sensor groups in response to the external operation, wherein the plurality of sensory inputs are in a plurality of sensory input signals;
generating an electrical input signal with a magnitude;
controlling the electrical input signal with the plurality of sensory inputs to create a plurality of sensory output signals collectively having a stimulus with a collective stimulus magnitude corresponding to the electrical input signal magnitude, each sensory output signal having a fraction of the stimulus magnitude corresponding to the fraction of the external operation magnitude sensed by one of the sensor groups; and
transmitting each of the sensory output signals to a designated one of each of a plurality of contacts through a designated one of a plurality of channels;
wherein controlling the output comprises:
processing the sensory input signals to create a plurality of control signals; and
controlling the electrical input signal with the control signals by applying the control signals to the electrical input signal to create the plurality of sensory output signals;
wherein the controlling the output step comprises digitally processing the electrical input signal with the plurality of sensory input signals;
wherein processing the sensory input signals comprises:
counting frequency pulse data in the sensory input signals within a discrete time frame; and
processing the frequency pulse data to determine the fraction of the stimulus magnitude to be generated in each of the sensory output signals;
wherein receiving the sensory input signals into a frequency counter comprises:
counting the frequency pulse data in the sensory input signals as binary values in a binary counter within a discrete time frame; and
storing the binary values for a delay time before transmitting the binary values.

4. A sensory feedback system for use with a prosthetic device comprising:
a power source adapted to transmit an electrical input signal;
a plurality of sensors each operable to create a sensory input in response to an external operation thereon;
a plurality of contacts each adapted to receive a sensory output signal;
a plurality of channels each connected to one of the plurality of contacts and adapted to carry one of the sensory output signals to the contact to which it is connected; and
a control and processing center adapted to receive the electrical input signal from the power source and to receive the sensory inputs from the sensors, to create the sensory output signals by processing the sensory inputs to create processed input signals and applying each of the processed input signals to the electrical input signal so that each sensory output signal has a particular stimulus with a particular stimulus level that corresponds to a particular processed input signal, and to transmit the sensory output signals to the contacts through the channels.

5. The sensory feedback system of claim 4 wherein the sensors comprise an inductance-based pressure sensor.

6. The sensory feedback system of claim 5 wherein the inductance-based pressure sensor is comprised of an inductance-based coil pressure sensor.

7. The sensory feedback system of claim 4 wherein the sensors comprise a resistance-based pressure sensor.

8. The sensory feedback system of claim 4 wherein the sensors comprise resistance-based pressure sensors having an electrical resistance, wherein the external operation comprises pressure, and wherein:

the control and processing center is adapted to deactivate the power source in response to resistance in each resistance-based pressure sensor which is greater than a selected level of electrical resistance and to activate the power source in response to resistance in any of the resistance-based pressure sensors which is less than the selected level of electrical resistance.

9. The sensory feedback system of claim 4 wherein the electrical input signal has a frequency and the sensory output signals have a frequency corresponding to the electrical input signal frequency, and wherein the sensory feedback system further comprises a frequency controller adapted to modify the frequency of the electrical input signal, thereby causing the frequency of the sensory output signals to be modified.

10. The sensory feedback system of claim 4 wherein one of the contacts comprises a floating ground contact.

11. The sensory feedback system of claim 4 wherein the control and processing center comprises an analog circuit.

12. The sensory feedback system of claim 11 wherein the electrical input signal has a magnitude and wherein the analog circuit comprises:

an oscillating circuit adapted to receive the electrical input signal from the power source and to oscillate the electrical input signal;

a transformer circuit adapted to receive the electrical input signal from the oscillator circuit and to increase the magnitude of a voltage; and a trigger circuit adapted to receive the electrical input signal from the transformer circuit and to apply each of the sensory inputs to the electrical input signal to create the sensory output signals.

13. The sensory feedback system of claim 4 wherein the control and processing center comprises an integrated circuit.

14. The sensory feedback system of claim 12 wherein each of the sensory output signals has a stimulus, and wherein the control and processing center comprises:

a processing center adapted to receive the sensory inputs from the sensors and to process the sensory inputs to create a plurality of control signals, each of the plurality of control signals designated to define the stimulus of one of the sensory output signals; and an isolator adapted to receive the plurality of control signals and to receive the electrical input signal, to apply the control signals to the electrical input signal to create the sensory output signals, and to transmit each of the sensory output signals through a designated one of the channels to a designated one of the contacts.

15. The sensory feedback system of claim 14 wherein the isolator is adapted to modify the frequency of the electrical input signal.

16. The sensory feedback system of claim 4 wherein the control and processing center comprises:

a frequency counter adapted to receive the sensory inputs within a designated time frame;

a process converter adapted to receive from the frequency counter the sensory inputs and to process the sensory inputs to create a plurality of control signals; and an isolator adapted to control an output of the electrical input signal, the isolator adapted to receive the electrical input signal from the power source, to receive the control signals from the process converter, and to apply the control signals to the electrical input signal to create the sensory output signals.

17. The sensory feedback system of claim 16 wherein the power source transmits an electrical power signal, and wherein the system further comprises:

a sensor controller adapted to receive the electrical power signal from the power source, to transmit the electrical power signal to the sensors, to receive the sensory inputs from the sensors as sensory input signals, and to transmit the sensory input signals to the process converter via the frequency counter.

18. The sensory feedback system of claim 17 wherein the process converter is adapted to select a designated one of the sensors to receive the electrical power signal and to generate a process control signal identifying the designated sensor, and wherein the sensor controller comprises:

an oscillator adapted to receive the electrical power signal and to oscillate the electrical power signal; and a multiplexer adapted to receive the oscillating electrical power signal from the oscillator, to receive a process control signal from the process converter, and, in response, to transmit the oscillating electrical power signal to the designated sensor.

19. The sensory feedback system of claim 17 wherein the power source comprises:

a battery adapted to transmit the electrical power signal and the electrical input signal, the electrical input signal having a magnitude; and a transformer circuit adapted to receive the electrical input signal, to oscillate the electrical input signal, to modify the magnitude of the electrical input signal, and to transmit the modified oscillating electrical input signal to the isolator.

20. The sensory feedback system of claim 19 wherein the process converter comprises:

a processor having a processing program and adapted to receive the sensory input signals from the frequency counter and to process the sensory input signals with the processing program to create intermediate control signals; and a converter adapted to receive the intermediate control signals from the processor, to translate the intermediate control signals into control signals that can be received and processed by the isolator, and to transmit the control signals to the isolator.

21. The sensory feedback system of claim 20 wherein:

the converter comprises a digital potentiometer adapted to transmit each of the intermediate control signals, each intermediate control signal having a designated voltage magnitude; and the isolator comprises an optical isolator adapted to receive the intermediate control signals and to convert the designated voltage magnitude of each intermediate control signal into a corresponding resistance value, to receive the electrical input signal, and to apply each of the resistance values to the electrical input signal to create the sensory output signals.

22. The sensory feedback system of claim 20 further comprising an option controller adapted to control a maximum magnitude and a minimum magnitude of a stimulus of the sensory output signals.

23. A sensory feedback system for a prosthetic device comprising:

a power source adapted to transmit an electrical power signal and an electrical input signal;

a control and processing center adapted to receive the electrical input signal and to transmit a plurality of sensory output signals;

a plurality of contacts each adapted to receive a designated one of the sensory output signals;

a plurality of inductance-based pressure sensors each adapted to receive the electrical power signal, to change the electrical power signal to a sensory input signal representing pressure applied thereto, and to transmit the sensory input signal therefrom; and a sensor controller adapted to route the electrical power signal to each inductance-based pressure sensor and to return the sensory input signal from each inductance-based pressure sensor to the control and processing center;

wherein the control and processing center is further adapted to process the sensory input signals and the electrical input signal to create a plurality of sensory output signals each representing the pressure applied to at least one of the inductance-based pressure sensors, and to transmit the sensory output signals to the contacts.

24. The sensory feedback system of claim 23 wherein the control and processing center selects a designated one of the sensors to receive the electrical input signal and transmits a processor control signal designating the sensor and wherein the sensor controller comprises:

an oscillator adapted to receive the electrical power signal and to oscillate the electrical power signal; and a multiplexer adapted to receive the oscillating electrical power signal from the oscillator, to receive the processor control signal from the control and processing center, and to transmit the oscillating electrical power signal to the designated sensor.

25. The sensory feedback system of claim 23 wherein the control and processing center is adapted to control the output of the electrical input signal by processing the sensory input signals to create a plurality of control signals and applying the control signals to the electrical input signal to create the sensory output signals.

26. The sensory feedback system of claim 25 wherein the electrical input signal has a voltage magnitude and wherein the control and processing system is adapted to apply the control signals to the electrical input signal to define a current magnitude in each of the sensory output signals.

27. The sensory feedback system of claim 25 wherein the electrical power signal has a frequency and wherein the control and processing center is adapted to control the frequency of the electrical power signal.

28. The sensory feedback system of claim 25 wherein one of the contacts is a floating ground contact adapted to return at least one of the sensory output signals to the control and processing center.

29. The sensory feedback system of claim 25 further comprising a sensor unit adapted to be fitted to a foot wherein the sensor unit comprises the sensors.

30. The sensory feedback system of claim 29 wherein the sensor unit comprises a foam rubber layer.

31. The sensory feedback system of claim 30 wherein the foam rubber layer comprises cellular urethane.

32. The sensory feedback system of claim 31 wherein the cellular urethane has a durometer value in a range of ten to thirty.

33. The sensory feedback system of claim 32 wherein the cellular urethane has a durometer value of approximately fifteen.

34. The sensory feedback system of claim 29 wherein the sensor unit further comprises a foil layer.

35. The sensory feedback system of claim 25 further comprising a prosthesis adapted to be fitted to a residual limb of an amputee wherein the prosthesis comprises the sensors.

36. The sensory feedback system of claim 35 further comprising a sensor unit which contains the sensors.

37. The sensory feedback system of claim 35 wherein the sensor unit comprises a foam rubber layer.

38. The sensory feedback system of claim 37 wherein the foam rubber layer comprises cellular urethane.

39. The sensory feedback system of claim 38 wherein the cellular urethane has a durometer value in a range of ten to thirty.

40. The sensory feedback system of claim 39 wherein the cellular urethane has a durometer value of approximately fifteen.

41. The sensory feedback system of claim 35 wherein the sensor unit further comprises a foil layer.

42. The sensory feedback system of claim 25 wherein the inductance-based pressure sensors comprise a front inductance-based pressure sensor and a back inductance-based pressure sensor, wherein the front pressure is applied to the front inductance based pressure sensor and the back pressure is applied to the back inductance based pressure sensor, and wherein the control and processing center is adapted to transmit sensory output signals to the contacts when the front pressure is not equal to the back pressure.

43. The sensory feedback system of claim 25 wherein the control and processing center comprises:

a frequency counter adapted to receive data in the sensory input signals within a designated time frame;

a process converter adapted to receive the data from the sensory input signals from the frequency counter and to process the data to create a plurality of control signals; and an isolator operable to control the output of the electrical input signal, the isolator adapted to receive the electrical input signal from the power source, to receive the control signals from the process converter, and to apply the control signals to the electrical input signal to create the sensory output signals.

44. The sensory feedback system of claim 43 wherein the power source transmits an electrical power signal, wherein the process converter selects a designated one of the sensors to receive the electrical input signal, and wherein the sensor controller comprises:

an oscillator adapted to receive the electrical power signal and to oscillate the electrical power signal; and a multiplexer adapted to receive the oscillating electrical power signal from the oscillator and to transmit the oscillating electrical power signal to the designated sensor.

45. The sensory feedback system of claim 44 wherein the power source comprises:

a battery adapted to transmit the electrical power signal and the electrical input signal, the electrical input signal having a magnitude; and a transformer circuit adapted to receive the electrical input signal, to oscillate the electrical input signal, to modify the magnitude of the electrical input signal, and to transmit the electrical input signal to the isolator.

46. The sensory feedback system of claim 45 wherein the process converter comprises:

a processor having a processing program and adapted to receive from the frequency counter the data from the sensory input signals and to process data with the processing program to create intermediate control signals; and a converter adapted to receive the intermediate control signals from the processor, to translate the intermediate control signals into control signals that can be received and processed by the isolator, and to transmit the control signals to the isolator.

47. The sensory feedback system of claim 46 wherein:

the converter comprises a digital potentiometer, the digital potentiometer transmitting each of the intermediate control signals, each intermediate control signal having a designated voltage magnitude; and the isolator comprises an optical isolator, the optical isolator adapted to receive the intermediate control signals and to convert each of the intermediate control signals having the designated voltage magnitude to a corresponding resistance value, to receive the electrical input signal, and to apply each of the resistance values to the electrical input signal to create the sensory output signals.

48. The sensory feedback system of claim 47 wherein the electrical input signal has a frequency and wherein the converter is adapted modify the frequency of the electrical input signal.

49. The sensory feedback system of claim 47 further comprising an option controller adapted to control a maximum magnitude and a minimum magnitude of a stimulus in the sensory output signals.

50. The sensory feedback system of claim 47 wherein one of the contacts is a floating ground contact.

51. The sensory feedback system of claim 23 wherein the control and processing center is adapted to transmit the sensory output signals to the contacts after the pressure applied to the inductance-based pressure sensors exceeds a pressure threshold.

52. The sensory feedback system of claim 23 wherein the control and processing center is adapted to transmit the sensory output signals to the contacts after pressure is applied to the inductance-based pressure sensors for a time exceeding a time threshold.

53. The sensory feedback system of claim 23 wherein:

the inductance-based pressure sensors comprise a front inductance-based pressure sensor and a back inductance-based pressure sensor;

the contacts comprise a front contact and a back contact, wherein the pressure comprises a total pressure comprising a front pressure and a back pressure;

the front pressure is applied to the front inductance based pressure sensor and the back pressure is applied to the back inductance based pressure sensor;

the control and processing center is adapted to transmit a front sensory output signal and a back sensory output signal collectively having a total magnitude; and the control and processing center is adapted to transmit the front sensory output signal to the front contact having a stimulus with a stimulus magnitude having a proportion of the total magnitude corresponding to a proportion of the front pressure with respect to the total pressure and to transmit the back sensory output signal to the back contact having a stimulus with a stimulus magnitude having a proportion of the total magnitude corresponding to a proportion of the back pressure with respect to the total pressure.

* * * * *